(12) United States Patent
Burchard

(10) Patent No.: US 7,371,516 B1
(45) Date of Patent: May 13, 2008

(54) METHODS FOR DETERMINING THE SPECIFICITY AND SENSITIVITY OF OLIGONUCLEO TIDES FOR HYBRIDIZATION

(75) Inventor: Julja Burchard, Kirkland, WA (US)

(73) Assignee: Rosetta Inpharmatics LLC, Seattle, WA (US)

( * ) Notice: Subject to any disclaimer, the term of this patent is extended or adjusted under 35 U.S.C. 154(b) by 382 days.

(21) Appl. No.: 09/616,849

(22) Filed: Jul. 14, 2000

Related U.S. Application Data

(60) Provisional application No. 60/144,382, filed on Jul. 16, 1999, provisional application No. 60/154,563, filed on Sep. 17, 1999.

(51) Int. Cl.
*C12Q 1/68* (2006.01)
*C12M 1/36* (2006.01)
*C07H 21/04* (2006.01)

(52) U.S. Cl. .............. 435/6; 435/287.2; 536/23.1

(58) Field of Classification Search .............. 435/6, 435/287.2; 422/50, 68.1; 536/23.1, 243, 536/26.6
See application file for complete search history.

(56) References Cited

U.S. PATENT DOCUMENTS

| | | | |
|---|---|---|---|
| 4,900,659 A * | 2/1990 | Lo et al. ................. | 435/6 |
| 4,946,778 A | 8/1990 | Ladner et al. .......... | 435/69.6 |
| 5,445,934 A | 8/1995 | Fodor et al. ............ | 435/6 |
| 5,510,270 A | 4/1996 | Fodor et al. ............ | 436/518 |
| 5,539,083 A | 7/1996 | Cook et al. ............. | 530/333 |
| 5,552,270 A | 9/1996 | Khrapko et al. ........ | 435/6 |
| 5,556,749 A | 9/1996 | Mitsuhashi et al. ..... | 435/6 |
| 5,556,752 A | 9/1996 | Lockhart et al. ....... | 435/6 |
| 5,569,588 A | 10/1996 | Ashby et al. ........... | 435/6 |
| 5,578,832 A | 11/1996 | Trulson et al. ......... | 250/458.1 |

(Continued)

FOREIGN PATENT DOCUMENTS

WO    WO 88/09810    12/1988

(Continued)

OTHER PUBLICATIONS

Lockhart et al "Expression monitoring by hybridization to high-density oligonucleotide arrays" Nature Biotechnology, 1996, 14: 1675-1680.*

(Continued)

*Primary Examiner*—B J Forman
(74) *Attorney, Agent, or Firm*—Jones Day

(57) ABSTRACT

The present invention provides materials and methods which may be used to evaluate one or more different probes and select probes that are optimized for sensitivity and specificity for a particular target. In particularly preferred embodiments, the methods and compositions of the invention can be used to evaluate polynucleotide probes having different nucleotide sequences. The methods and compositions thereby allow a user to select a polynucleotide probe, e.g., having a particular nucleotide sequence, that is optimized for sensitivity and/or for specificity for a particular target polynucleotide molecule. In particularly preferred embodiments, the methods and compositions can be used to evaluate a plurality of probes simultaneously, such as on a microarray.

Probes evaluated according to the methods of the invention can be selected for and used to detect a variety molecules, including a variety of polynucleotides, such as genomic polynucleotides (e.g., genomic DNA) and genomic transcripts (e.g., mRNAs or cDNA sequences derived from there) as well as gene copy numbers of specific transcripts, single nucleotide polymorphisms, etc.

53 Claims, 6 Drawing Sheets

U.S. PATENT DOCUMENTS

| | | | | |
|---|---|---|---|---|
| 5,716,785 | A | 2/1998 | van Gelder et al. | 435/6 |
| 5,723,320 | A | 3/1998 | Dehlinger | 435/91.1 |
| 5,744,305 | A | 4/1998 | Fodor et al. | 435/6 |
| 5,807,522 | A * | 9/1998 | Brown et al. | 422/50 |
| 5,817,461 | A | 10/1998 | Austin et al. | 435/6 |
| 5,837,832 | A | 11/1998 | Chee et al. | 536/22.1 |
| 5,856,103 | A | 1/1999 | Gray et al. | 435/6 |
| 5,965,352 | A | 10/1999 | Stoughton et al. | 435/4 |
| 6,027,890 | A | 2/2000 | Ness et al. | 435/6 |
| 6,040,138 | A | 3/2000 | Lockhart et al. | 435/6 |
| 6,110,676 | A | 8/2000 | Coull et al. | 435/6 |
| 6,132,969 | A | 10/2000 | Stoughton | 435/6 |
| 6,146,593 | A | 11/2000 | Pinkel et al. | 422/68.1 |
| 6,146,830 | A | 11/2000 | Friend et al. | 435/6 |
| 6,156,502 | A | 12/2000 | Beattie | 435/6 |
| 6,171,794 | B1 | 1/2001 | Burchard et al. | 435/6 |
| 6,218,122 | B1 | 4/2001 | Friend et al. | 435/6 |
| 6,251,601 | B1 * | 6/2001 | Bao et al. | 435/6 |
| 6,271,002 | B1 | 8/2001 | Lingsley et al. | 435/91.1 |
| 6,344,316 | B1 * | 2/2002 | Lockhart | |

FOREIGN PATENT DOCUMENTS

| | | |
|---|---|---|
| WO | WO 90/11364 | 10/1990 |
| WO | WO 98/38329 | 9/1998 |
| WO | WO 98/41531 | 9/1998 |
| WO | WO 99/11820 | 3/1999 |
| WO | WO 00/43942 | 7/2000 |
| WO | WO 00/53811 | 9/2000 |

OTHER PUBLICATIONS

U.S. Appl. No. 09/303,082, filed Apr. 30, 1999, Friend and Stoughton.
U.S. Appl. No. 09/364,751, filed Jul. 20, 1999, Friend et al.
U.S. Appl. No. 09/408,582, filed Sep. 29, 1999, Stoughton et al.
U.S. Appl. No. 60/084,742, filed May 8, 1998, Friend and Stoughton.
U.S. Appl. No. 60/090,046, filed Jun. 19, 1998, Friend and Stoughton.
Albretsen et al., 1988, "Optimal conditions for hybridization with oligonucleotides: a study with myc-oncogene DNA probes", Anal Biochem 170:193-202.
Altschul et al., 1990, J. Mol. Biol. 215:403-410.
Altschul et al., 1997, Nucl. Acids Res. 25:3389-3402.
Anderson et al., 1994, Adv. Immunol. 56:171-178.
Anshelevich VV et al., 1984, "Slow relaxational processes in the melting of linear biopolymers: a theory and its application to nucleic acids", Biopolymers. Jan.;23(1):39-58.
ATCC T1B-152.
ATCC CCL-243.
Beattie et al., 1995, "Hybridization of DNA targets to glass-tethered oligonucleotide probes", Mol Biotechnol 4:213-225.
Belshaw et al., 1996, Proc. Natl. Acad. Aci. USA 93:4604-4607.
Bernoist and Chambon, 1981, Nature 290:304-310.
Biocca and Cattanco, 1995, Trends Cell Biol. 5:248-252.
Blanchard et al., 1996, Nat. Biotech. 14:1649.
Blanchard et al., 1996, Biosensors and Bioelectronics 11:687-690.
Blanchard, 1998, "Synthetic DNA Arrays" in *Genetic Engineering* (Plenum Press, New York) vol. 20 pp. 111-123.
Boguski and Schuler, 1995, Nat. Gen. 10:369-371.
Bradbury et al., 1995, *Antibody Engineering* (IRL Press) vol. 2 pp. 295-361.
Brinster et al., 1982, Nature 296:39-42.
Burke et al., 1984, Cell 36:847-858.
Bussey et al., 1995, Proc. Natl. Acad. Sci. USA 92:3809-3813.
Cech et al., 1987, Science 236:1532-1539.
Chetverin and Kramer, 1994, Bio/Technology 12:1093-1099.
Chirgwin et al., 1979, Biochem. 18:5294-5299.
Claverie, 1996, Meth. Enzymol. 266:212-227.
Cole et al., 1985, *Monoclonal Antibodies and Cancer Therapy* (Alan R. Liss, Inc.) pp. 77-96.
Cotten and Birnstiel, 1989, EMBO J. 8:3861-3866.
DeRisi et al., 1996, Nat. Gen. 14:457-460.
Dohmen et al., 1994, Science 263:1273-1276.
Dujon et al., 1994, Nature 369:371-378.
Egholm et al., 1993, Nature 363:566-568.
Feldman et al., 1994, EMBO J. 13:5795-5809.
Ferguson et al., 1996, Nat. Biotech. 14:1681-1684.
Fodor et al., 1991, Science 251:767-773.
Froehler et al., 1986, Nucl. Acids Res. 14:5399-5407.
Galibert et al., 1996, EMBO J. 15:2031-2049.
Gari et al., 1997, Yeast 13:837-848.
Gautier et al., 1987, Nucl. Acids Res. 15:6625-6641.
Gibson, 1996, Cancer and Metastasis Rev. 15:287-299.
Goffeau et al., 1996, Science 274:546-567.
Good et al., 1997, Gene Ther. 4:45-54.
Gossen et al., 1995, Proc. Natl. Acad. Sci. USA 89:5547-5551.
Grassi and Marini, 1996, Ann. Med. 28:499-510.
Griffiths et al., 1994, EMBO J. 13:3245-3260.
Guo, 1996, Dissertation, University of Wisconsin.
Guo et al., 1997, "Enhanced discrimination of single nucleotide polymorphisms by artificial mismatch hybridization", Nat Biotechnol 15:331-335.
Haseloff and Gerlach, 1988, Nature 334:585-591.
Hayden et al., 1997, Curr. Opin. Immunol. 9:210-212.
Hershkowitz, 1987, Nature 329:219-222.
Hoffman et al., 1996, Proc. Natl. Acad. Sci. USA 83:5185-5190.
Hoffman et al., 1997, Nucl. Acids. Res. 25:1078-1079.
Huse et al., 1989, Science 246:1275-1281.
Hyndman et al., 1996, Biotechniques 20:1090-1096.
Ikuta et al., 1987, "Dissociation kinetics of 19 base paired oligonucleotide-DNA duplexes containing different single mismatched base pairs", Nucleic Acids Res 15:797-811.
Inoue et al., 1987, Nucl. Acids Res. 15:6131-6148.
Inoue et al., 1987, FEBS Lett. 215:327-330.
Johnston et al., 1994, Science 265:2077-2082.
Johnston et al., 1984, Mol. Cell. Biol. 4:1440-1448.
Kajimura et al., 1990, "Application of long synthetic oligonucleotides for gene analysis: effect of probe length and stringency conditions on hybridization specificity", Genet Anal Tech Appl 7:71-79.
Kerjan et al., 1986, Nucl. Acids Res. 14:7861-7871.
Khrapko et al., 1991, J. DNA Sequencing and Mapping 1:375-388.
Khrapko et al. 1991, Molecular Biology 25:581-591.
Khrapko, 1999, "Harvard Nathan Shock Center: High Throughput Technology Core" http://www.hms.harvard.edu/aging/nathan/high.html.
Khrapko et al., 1999, Poster Abstract, Chips to Hits '99 Conference, Nov. 2-5, 1999.
Ko et al., 1993, Mol. Cell. Biol. 13:638-648.
Kohler and Milstein, 1975, Nature 256:495-497.
Koizumi et al., 1988, FEBS Lett. 239:285-288.
Koizumi et al., 1988, FEBS Lett. 228:228-230.
Kozbor and Roder, 1983, Immunol. Today 4:72.
Lemaitre et al., 1989, Proc. Natl. Acad. Sci. USA 84:648-652.
Lipshutz et al., 1999, Nature Genetics Supplement 21:20-24.
Lockhart et al., 1996, Nat. Biotech. 14:1675-1680.
Lodish et al., 1995, *Molecular Biology of the Cell* (W.H. Freeman and Co., New York) Chapter 8.
Marks et al., 1992, J. Biol. Chem. 267:16007-16010.
Mascorro-Gallardo et al., 1996, Gene 172:169-170.
Maskos and Southern, 1992, Nucl. Acids Res. 20:1679-1684.
McBride and Caruthers, 1983, Tertahedron Lett. 24:245-248.
McGall et al., 1996, Proc. Natl. Acad. Sci. USA 93:13555-13560.
Miyoshi et al., 1995, Nucl. Acids Res. 23:2762-2769.
Morgan et al., 1988, Immunol. Today 9:84-86.
Morrison et al., 1984, Proc. Natl. Acad. Sci. USA 81:6851-6855.
Mumberg et al., 1994, Nucl. Acids Res. 22:5767-5768.
Neuberger et al. 1984, Nature 312:604-608.
Nguyen et al., 1995, Genomics 29:207-216.
Nicoloso et al., 1989, "Titration of variant DNA sequences differing by a single point-mutation by selective dot-blot hybridization with synthetic oligonucleotides", Biochem Biophys Res Comm 159:1233-1241.

Niemeyer et al., 1998, "Hybridization characteristics of biomolecular adaptors, covalent DNA—streptavidin conjugates", Bioconjug Chem 9:168-175.
No et al., 1996, Proc. Natl. Acad. Sci. USA 93:3346-3351.
Nocka et al., 1990, EMBO J. 9:1805-1813.
Paulus et al., 1996, J. Virol. 70:62-67.
Pease et al., 1994, Proc. Natl. Acad. Sci. USA 91:5022—5026.
Perlmutter and Alberola, 1996, Curr. Opin. Immunol. 8:285-290.
Persson et al., 1997, "Analysis of oligonucleotide probe affinities using surface plasmon resonance: a means for mutational scanning", Anal Biochem 246:34-44.
Pettitt et al., 1996, Dev. 122:4149-4157.
Press et al., 1992, "Solution of Linear Algebraic Equations" *Numerical Recipes in C* (Cambridge University Press) Chapter 2.
Ramirez-Solis et al., 1993, Meth. Enzymol. 225:855-878.
Ray et al., 1997, Proc. Natl. Acad. Sci. USA 94:3229-3234.
Santa Lucia, 1998, Proc. Natl. Acad. Sci. USA 95:1460-1465.
Sarin et al., 1988, Proc. Natl. Acad. Sci. USA 85:7448-7451.
Sarver et al., 1990, Science 247:1222-1225.
Schena et al., 1996, Proc. Natl. Acad. Sci. USA 93:10614.
Schena et al., 1995, Science 270:467-470.
Schuler, 1997, J. Mol. Med. 75:694-698.
Schuler et al., 1996, Science 274:540-546.
Shalon et al., 1996, Genome Res. 6:639-645.
Shimizu et al., 1992, J. Biochem. 111:272-277.
Southern et al., 1994, Nucl. Acids. Res. 22:1368-1373.
Southern et al., 1992, Genomics 13:1008-1017.
Spencer, 1996, Trends Gen. 12:181-187.
Spradling et al., 1995, Proc. Natl. Acad. Sci. USA 92:10824-10830.
Stein et al., 1988, Nucl. Acids Res. 16:3209.
Stimpson et al., 1995, "Real-time detection of DNA hybridization and melting on oligonucleotide arrays by using optical wave guides", Proc Natl Acad Sci USA 92:6379-6383.
Straus and Weiss, 1992, Cell 70:585-593.
Takeda et al., 1985, Nature 314:452-454.
Thomas and Capecchi, 1987, Cell 51:503-512.
van der Krol et al., 1988, BioTechniques 6:958-976.
Vernier et al., 1996, "Radioimager quantification of oligonucleotide hybridization with DNA immobilized on transfer membrane: application to the identification of related sequences", Anal Biochem 235:11-19.
Wagner et al., 1981, Proc. Natl. Acad. Sci. USA 78:1441-1445.
Wang et al., 1995, "Origins of high sequence selectivity: a stopped-flow kinetics study of DNA/RNA hybridization by duplex- and triplex-forming oligonucleotides", Biochem 34:9774-9784.
Wetmur, 1991, "DNA probes: applications of the principles of nucleic acid hybridization", Crit Rev Biochem Mol Biol 26:227-259.
www.ncbi.nlm.nih.gov Genbank Accession U83115. Human non-lens beta gamma-crystallin like protein (AIM1) mRNA, partial cds.
www.ncbi.nlm.nih.gov Genbank Accession U18778. Saccharomyces cerevisiae chromosome V cosmids 9537, 9581, 9495, 9867, and lambda clone 5898.
www.ncbi.nlm.nih.gov Genbank Accession D43968. Human AML1 mRNA for AML1b protein (alternatively spliced product), complete cds.
www.ncbi.nlm.nih.gov Genbank Accession M62829. Human transcription factor ETR103 mRNA, complete cds.
Yamamoto et al., 1980, Cell 22:787-797.
Young and Wagner, 1991, "Hybridization and dissociation rates of phosphodiester or modified oligodeoxynucleotides with RNA at near-physiological conditions", Nucleic Acids Res 19:2463-2470.
Zhang and Madden, 1997, Genome Res. 7:649-656.
Zon, 1988, Pharm. Res. 5:539-549.

* cited by examiner

METHODS FOR DETERMINING THE SPECIFICITY AND SENSITIVITY OF OLIGONUCLEO TIDES FOR HYBRIDIZATION

This application claims the benefit of U.S. Provisional Patent Application Ser. No. 60/144,382, filed on Jul. 16, 1999 and U.S. Provisional Patent Application Ser. No. 60/154,563, filed on Sep. 17, 1999, each of which is incorporated by reference herein in its entirety.

1. FIELD OF THE INVENTION

The field of this invention relates to the field of detecting and reporting polynucleotide sequences, including genomic sequences, genomic transcript sequences (e.g., mRNAs from cells and/or cDNA sequences derived therefrom) copy numbers and single nucleotide polymorphisms (SNPs), by nucleic acid hybridization, e.g., on nucleic acid microarrays. In particular, the invention relates to methods for identifying and/or selecting polynucleotide sequences, particularly oligonucleotide sequences, which may be used as hybridization probes (e.g., on nucleic acid microarrays) that are both sensitive and specific to particular target polynucleotide sequences of interest.

2. BACKGROUND

Within the past decade, several technologies have made it possible to monitor the expression level of a large number of genetic transcripts at any one time (see, e.g., Schena et al., 1995, *Science* 270:467-470; Lockhart et al., 1996, *Nature Biotechnology* 14:1675-1680; Blanchard et al., 1996, *Nature Biotechnology* 14:1649; Ashby et al., U.S. Pat. No. 5,569,588, issued Oct. 29, 1996). For example, techniques are known for preparing microarrays of cDNA transcripts (see, e.g., DeRisi et al., 1996, *Nature Genetics* 14:457-460; Shalon et al., 1996, *Genome Res.* 6:689-645; and Schena et al., 1995, *Proc. Natl. Acad. Sci. U.S.A.* 93:10539-11286). Alternatively, high-density arrays containing thousand of oligonucleotides complementary to defined sequences, at defined locations on a surface using photolithographic techniques for synthesis in situ are described, e.g., Fodor et al., 1991, *Science* 251:767-773; Pease et al., 1994, *Proc. Natl. Acad. Sci. U.S.A.* 91:5022-5026; Lockhart et al., 1996, *Nature Biotechnology* 14:1675; U.S. Pat. Nos. 5,578,832; 5,556,752; and 5,510,270). Methods for generating arrays using inkjet technology for oligonucleotide synthesis are also known in the art (see, e.g., Blanchard, International Patent Publication WO 98/41531, published Sep. 24, 1998; Blanchard et al., 1996, *Biosensors and Bioelectronics* 11:687-690; Blanchard, 1998, in *Synthetic DNA Arrays in Genetic Engineering*, Vol. 20, J. K. Setlow, Ed., Plenum Press, New York at pages 111-123).

Applications of this technology include, for example, identification of genes which are up regulated or down regulated in various physiological states, particularly diseased states. Additional exemplary uses for transcript arrays include the analyses of members of signaling pathways, and the identification of targets for various drugs. See, e.g., Friend and Hartwell, International Publication No. WO 98/38329 (published Sep. 3, 1998); Stoughton, U.S. patent application Ser. No. 09/099,722 (filed Jun. 19, 1998); Stoughton and Friend, U.S. patent application Ser. No. 09/074,983 (filed May 8, 1998); Friend and Stoughton, U.S. Provisional Application Ser. Nos. 60/084,742 (filed May 8, 1998), 60/090,004 (filed Jun. 19, 1998), and 60/090,046 (filed Jun. 19, 1998).

Oligonucleotide sequences are particularly useful as probes on microarrays and in other applications that involve nucleic acid hybridization. The oligonucleotides can be custom synthesized, by techniques known in the art (see, e.g., Froehler et al., 1986, *Nucleic Acid Res.* 14:5399-5407; McBride et al., 1983, *Tetrahedron Lett.* 24:246-248), with any desired DNA sequence. Further, oligonucleotides are small enough that their thermodynamic properties (e.g., their free binding energies to complementary and/or partially complementary sequences) can be at least partially predicted. However, because of their small size, oligonucleotide probes frequently correspond to genomic sequences that are non-unique and, as a result, may hybridize to more than one polynucleotide sequence in a sample. For example, a particular oligonucleotide probe may not only hybridize to a particular mRNA transcript of interest in a sample, but may also hybridize to other homologs, analogs, splice variants or even marginally related sequence of that transcript that are also, often times in greater abundances, in a sample. As a result of such "cross-hybridization," many oligonucleotide probes can result in false positive measurement, reflecting a lack of specificity. Conversely, an oligonucleotide probe may also hybridize to a target polynucleotide sequence of interest more weakly than predicted, e.g., from predicted hybridization binding energies. Such probes can result in false negative hybridization measurements, reflecting a lack of sensitivity.

As a result of these limitations, current microarrays require a plurality of probe pairs, which are both matched to and intentionally mismatched to a target sequence, in order to empirically distinguish signal arising from a target polynucleotide sequence of interest (e.g., a particular mRNA sequence of interest) from signal arising from cross-hybridization with other polynucleotide sequences. Currently, in situ synthesized microarray chips require more than 20 oligonucleotide probe pairs per gene or gene region reported (Lockhart et al., supra). However, unless a large number of probes is employed, such a match-mismatch scheme can only screen out cross-hybridization from distantly related sequences. In particular, the ability of such a match-mismatch scheme to distinguish between true hybridization and cross-hybridization to closely related sequences (e.g., closely related homologs and splice variants) is typically limited or even very poor. Furthermore, the "reporting density" (i.e., the number of genes detected per unit of surface area) for a microarray is limited, e.g., by the density with which polynucleotide probes may be laid down as well as by the number of polynucleotide probes required per gene. The number of polynucleotide probes that may be laid down on a microarray chip is therefore limited by the technology used to produce the microarray. Photolithographic techniques discussed above for producing oligonucleotide microarrays having a high spatial density of probes are expensive to synthesize and therefore require a large capital investment. Oligonucleotide microarrays produced using the above discussed inkjet technology methods are, by contrast, much cheaper and faster to produce both per chip design and per chip. Thus, such microarrays are generally preferred for detecting genetic transcripts in cells. However, microarray chips produced by such inkjet technology have a limited probe density that is only a fraction of the probe density of chips produced by photolithography methods. Thus, because microarrays currently known in the art must use a number of redundant probes (e.g., 20) and have limited probe density, the number of genetic transcripts that may be effectively detected on a single microarray chip is limited to about 10,000 gene transcripts using expensive, photolithographic arrays, and only about 750 to 2,500 gene transcripts using less expensive, inkjet arrays.

There exists, therefore, a need for methods which identify particular oligonucleotide sequences that may be used as both sensitive and specific probes for target polynucleotide sequences. In particular, there is a need for methods that can identify particular sequences that hybridize to a particular sequence of interest, such as the sequence of a particular gene or gene transcript, with little or no cross-hybridization to other polynucleotide sequences in a sample. There is also a need for methods to design nucleic acid arrays which have less require fewer polynucleotide probe sequences to detect individual genes of interest, and which therefore contain polynucleotide probe sequences to detect more genes of interest than do microarrays that a currently available in the art.

Discussion or citation of a reference herein shall not be construed as an admission that such reference is prior art to the present invention.

3. SUMMARY OF THE INVENTION

The present invention provides compositions and methods that can be used to evaluate binding properties of molecules of a first type, which are referred to herein as probe molecules, to molecules of a second type, which are referred to herein as target molecules. Specifically, the methods and compositions of the invention can be used to evaluate both the sensitivity and the specificity with which a probe binds to a particular target.

The sensitivity of a probe, as the term is used herein, is understood to refer to the absolute amount or level of a particular target (i.e., the number of molecules of the particular target) that binds to the probe under particular binding conditions. The amount or level of a particular target that binds to a probe under particular binding conditions is also referred to herein as the amount or level of specific binding to the probe under the particular binding conditions.

The specificity of a probe, as the term is used herein, is understood to refer to the amount or level of a particular target (i.e., the number of molecules of the particular target) that binds to the probe under particular binding conditions relative to the amount or level of non-specific binding to the probe under the same binding conditions. Non-specific binding, as the term is used herein, is understood to refer to the amount of molecules other than molecules of the particular target (i.e., the number of molecules that are not molecules of the particular target) that bind to the probe under particular binding conditions.

The methods of the invention involve comparing the amount or number of molecules in a first sample that bind to molecules of a probe to the amount or number of molecules in a second sample that bind to molecules of the same probe. The first sample, which is referred to herein as a "specific binding sample," preferably comprises molecules of a particular target that is generally a target of interest to a user. Preferably, the molecules of the particular target in the specific binding sample are substantially pure (e.g., at least 75% pure, preferably at least 90% pure, more preferably at least 95% pure and even more preferably 99% pure).

The second sample, which is referred to herein as a "non-specific binding sample," comprises molecules of a plurality of different (i.e., non-identical) targets other than the particular target of interest. Preferably, the molecules of the plurality of different targets are of the same type and approximately the same abundances as molecules in a real sample for which the probe is intended.

The invention is based, at least in part, on the discovery that a meaningful measurement of nonspecific binding to molecules of a particular probe may be obtained by supplying a distinguishable binding sample of competing molecules in which the competing molecules are of the same type and have approximately the same abundances as competing molecules in a real sample for which the particular probe is intended. Such binding samples may be readily obtained, e.g., according to the methods of the invention described hereinbelow, and can be used as non-specific binding samples in the methods of the invention to obtain a real measurement of non-specific binding that can be readily compared to measurements of specific binding from a specific binding sample. Indeed, the methods of the invention both the specific and non-specific binding levels to be measured simultaneously. The specific and non-specific binding samples need not be physically separate but need only be distinct from one another so that the binding of molecules from the specific binding sample can be distinguished from the binding of molecules from the non-specific binding sample. For example, in a preferred embodiment the specific and non-specific binding samples are differentially labeled, e.g., with fluorescent labels that fluoresce at different wavelengths.

The methods of the invention are particularly useful for evaluating large numbers of different probes. For example, the methods of the invention can be used to evaluate a plurality of different probes by comparing the amount or number of molecules from a first sample (i.e., a specific binding sample) that bind to a each of the plurality of different probes to the number or amount of molecules from a second sample (i.e., a non-specific binding sample) that bind to each of the plurality of different probes. In preferred embodiments, the methods of the invention are used to evaluate a plurality of different probes in an array of probes, wherein the array comprises a solid (or, in certain embodiments, semi-solid) support or surface to which molecules of the plurality of different probes are immobilized. Most preferably, the array is an addressable array, such as a positionally addressable array wherein each different probe is located at a specific, known location on the support or surface such that the identity of a particular probe can be determined from its location on the support or surface.

The probes and target molecules that can be evaluated using the compositions and methods of the invention can be of any type, although they are preferably molecules of a type or class that can specifically bind to one another. For example, in certain embodiments, the probes can be molecules of a particular antibody (preferably a monoclonal antibody) and the target molecules can be molecules to which antibodies can specifically bind such as proteins. However, the compositions and methods of the invention are particularly useful for evaluating the hybridization properties of different polynucleotide probes to examine both the sensitivity and specificity with which the polynucleotide probes hybridize to particular target polynucleotides (i.e., to polynucleotide molecules having particular nucleotide sequences). Thus, in preferred embodiments of the invention both the probes and the target molecules are polynucleotide molecules.

In such preferred embodiments, the sensitivity of a probe is understood to refer to the absolute amount of a particular target polynucleotide (i.e., the number of polynucleotide molecules having a particular nucleotide sequence) that hybridizes to the probe under particular hybridization conditions. The amount of a particular target polynucleotide that hybridizes to a probe under particular hybridization conditions is also referred to herein as the amount of specific hybridization to the probe under the particular hybridization conditions.

The specificity of a probe, as the term is used in preferred embodiments of the invention, is understood to refer to the amount of a particular target polynucleotide (i.e., the number of polynucleotide molecules having a particular nucleotide sequence) that hybridizes to the probe under particular hybridization conditions compared to or relative to the amount of cross hybridization to the probe under the same hybridization conditions.

Cross-hybridization or non-specific hybridization, as the terms are used herein, are understood to refer to the amount of polynucleotides other than the particular target polynucleotide (i.e., the number of polynucleotide molecules having nucleotide sequences that are different than the nucleotide sequence of the particular target polynucleotide) that hybridize to the probe under particular hybridization conditions.

In particularly preferred embodiments, the methods of the invention involve comparing the number or amount of polynucleotide molecules from a first sample that hybridize to molecules of a polynucleotide probe to the number or amount of polynucleotide molecules from a second sample that hybridize to molecules of the polynucleotide probe. The first sample is a "specific hybridization sample" comprising molecules of a particular target polynucleotide (i.e., polynucleotide molecules having a particular sequence). The polynucleotide sequence can be, for example, the sequence of a particular gene or gene transcript of a cell or organism. The second sample is a "non-specific hybridization sample" comprising a plurality of different (i.e., non-identical) polynucleotide molecules, each different polynucleotide molecule having a different nucleotide sequence. In particular, the second or non-specific hybridization sample should comprise polynucleotide molecules having nucleotide sequences that are different from the nucleotide sequence of the particular target polynucleotide in the first or specific hybridization sample. For example, in embodiments wherein the sequence of the particular target polynucleotide in the first or specific hybridization sample is the sequence of a particular gene or gene transcript of a cell or organism, the nucleotide sequences of the polynucleotide molecules in the second, non-specific hybridization sample preferably comprise sequences representing the other genes or gene transcripts of the cell or organism.

For example, the invention provides a first preferred embodiment wherein the first sample (i.e., the specific hybridization sample) is a substantially pure (i.e., at least 75% pure, preferably at least 90% pure and more preferably at least 95% or 99% pure) sample of molecules having a particular target nucleotide sequence and the second sample (i.e., the non-specific hybridization sample) comprises a plurality of different polynucleotide molecules, with each different polynucleotide molecule is the second sample having a different nucleotide sequence. In a particularly preferred aspect of this first preferred embodiment, the target polynucleotide molecules is a gene or gene transcript (e.g., a mRNA or cDNA molecule) of a cell or organism and the non-specific hybridization sample is a polynucleotide sample from a "deletion mutant" of the cell or organism (i.e., a variety or strain of the cell or organism in which the gene or gene transcript corresponding to the target polynucleotide is absent or is silent and not expressed).

The invention also provides a second preferred embodiment wherein the first sample (i.e., the specific hybridization sample) is a substantially pure sample of molecules having a particular target nucleotide sequence and the second sample (i.e., the non-specific hybridization sample) comprises a plurality of different polynucleotide molecules with each different polynucleotide molecule in the second sample having a different nucleotide sequence. In particular, in the second preferred embodiment of the invention, the polynucleotide molecules in the non-specific hybridization sample include molecules of the target polynucleotide sequence. In a particularly preferred aspect of this second preferred embodiment, the target polynucleotide corresponds to a gene or gene transcript of a cell or organism and the non-specific hybridization sample is a polynucleotide sample from the "wild type" cell or organism which expresses the gene or gene transcript corresponding to the target polynucleotide at normal levels or amounts.

The invention further provides a third preferred embodiment wherein the first sample (i.e., the specific hybridization sample) comprises molecules having a particular target polynucleotide sequence as well as molecules having other non-target polynucleotide sequences and the second sample (i.e., the non-specific hybridization sample) comprises a plurality of different non-target polynucleotide molecules. Thus, in the third preferred embodiment of the invention, the specific hybridization sample is identical to the non-specific hybridization sample described above for the second preferred embodiment of the invention, and the non-specific hybridization sample is identical to the non-specific hybridization sample described above for the first preferred embodiment of the invention.

The invention still further provides a forth preferred embodiment wherein both the first and second sample (i.e., the specific and the non-specific hybridization samples) comprise a plurality of different polynucleotide molecules, including molecules of the target polynucleotide. However, in the forth preferred embodiment of the invention the amount or level of molecules of the target polynucleotide in the first, specific hybridization sample differs substantially from the amount or level of molecules of the target polynucleotide in the second, non-specific hybridization sample.

Although the probes used in the invention can comprise any type of polynucleotide, in preferred embodiments the probes comprise oligonucleotide sequences; i.e., polynucleotide sequences that are between about 4 and about 200 bases in length, and are most preferably between about 15 and about 150 bases in length. In one embodiment, shorter oligonucleotide sequences are used that are less than about 40 bases in length, and are more preferably between about 15 and about 30 bases in length. However, a preferred embodiment of the invention uses longer oligonucleotide probes that are between about 40 and about 80 bases in length with oligonucleotide sequences between about 50 and about 70 bases in length (e.g., oligonucleotide sequences of about 50 to about 60 bases in length) being particularly preferred.

The compositions and methods of the invention can also be used to evaluate different binding conditions for a probe or for a plurality of different probes. For example, the compositions and methods of the invention can be used to evaluate hybridization conditions for a polynucleotide probe or for a plurality of different polynucleotide probes. Specifically, the amount of binding of molecules from a first binding sample (i.e., a specific binding sample) to one or more different probes under particular binding conditions can be compared to the amount of binding of molecules from a second binding sample (i.e., a non-specific binding sample) to the one or more different probes under the same binding conditions. The sensitivity and specificity of the probe or probes under the particular binding conditions can then be readily determined. Thus, by performing the above comparison under different binding conditions (e.g., under different hybridization conditions for polynucleotides) optimum binding conditions can be readily ascertained, e.g., by determining the binding conditions wherein the sensitivity and specificity of the probe or probes to the particular target are optimized.

The invention therefore provides, in a first embodiment, a method for evaluating a probe comprising comparing the amount of binding of a first sample to the probe with the amount of binding of a second sample to the probe. The first sample comprises molecules of a particular target and the second sample comprises molecules of a plurality of different targets. In one preferred aspect of this first embodiment, the first sample is a substantially pure sample of molecules of the particular target (e.g., at least 75%, at least 90%, at least 95% or at least 99% pure). In another aspect of this first embodiment, each different target in the plurality of different targets of the second sample is different from the particular target of the first sample. In still other preferred aspects of this embodiment, the methods also determine the specificity of the probe, preferably from the ratio of the amount of binding of molecules of the particular target in the first sample to the probe with the amount of binding of molecules of the plurality of targets in the second sample to the probe. The invention still further provides aspects of this first embodiment wherein the molecules of the first and/or second samples are detectably labeled, e.g., with a fluorescent molecule. In particularly preferred aspects, the molecules of the particular target in the first sample are detectably labeled with a first label, and the molecules of the plurality of targets in the second sample are detectably labeled with a second, different label (e.g., with a first and second fluorescent molecule). In preferred aspects of this embodiment, the probe is attached to a surface of a support. In other preferred aspects, the probe is one of a plurality of probes, preferably wherein the plurality of probes comprises an array of probes, said array having a support with at least one surface and wherein each probe is attached to the surface of the support.

Aspects of this first embodiment are also provided wherein the probe is a polynucleotide probe having a particular nucleotide sequence. In various other aspects provided by the invention, the molecules of the particular target in the first sample are polynucleotide molecules having a nucleotide sequence. In particularly preferred aspects, the polynucleotide probe is attached to a surface of a support. In other preferred aspects the polynucleotide probe is one of a plurality of polynucleotide probes and, preferably, the plurality of polynucleotide probes comprises an array of polynucleotide probes, said array having a support with at least one surface wherein each polynucleotide probe is attached to the surface of the support.

The invention also provides, in another embodiment, a method for evaluating a polynucleotide probe having a particular nucleotide sequence, said method comprising comparing the amount of hybridization of a first sample to the polynucleotide probe with the amount of hybridization of a second sample to the polynucleotide probe, wherein: the first sample comprises molecules of a target polynucleotide having a target nucleotide sequence; and the second sample comprises a plurality of different polynucleotide molecules wherein each different polynucleotide molecule has a different nucleotide sequence. In one preferred aspect of this other embodiment, the first sample is a substantially pure sample of molecules of the target polynucleotide (e.g., at least 75%, 90%, 95% or 99% pure). In one aspect, each different polynucleotide molecule in the second sample has a nucleotide sequence different from the target nucleotide sequence. In another aspect, the plurality of different polynucleotide molecules in the second sample comprises: (a) polynucleotide molecules having a nucleotide sequence that is the same as the target nucleotide sequence, and (b) a plurality of different polynucleotide molecules each having a different nucleotide sequence that is different from the target nucleotide sequence. In another aspect, the first sample further comprises polynucleotide molecules having a nucleotide sequence different from the target nucleotide sequence. In one aspect, each different polynucleotide molecule in the second sample has a nucleotide sequence different from the target nucleotide sequence. In another aspect, the second sample comprises: (a) polynucleotide molecules having a nucleotide sequence that is the same as the target nucleotide sequence; and (b) a plurality of different polynucleotide molecules, each different polynucleotide molecule having a different nucleotide sequence that is different from the target nucleotide sequence, wherein the amount of polynucleotide molecules in the first sample having the target nucleotide sequence differs substantially from the amount of polynucleotide molecules in the second sample having the target nucleotide sequence (e.g., by a factor of at least two, at least four, at least eight, at least twenty, or at least 100).

The invention also provides, in still other embodiments, a method for evaluating a plurality of polynucleotide probes wherein each polynucleotide probe in the plurality of polynucleotide probes has a particular nucleotide sequence. The method comprises comparing the amount of hybridization of a first sample to each polynucleotide probe in the plurality of polynucleotide probes with the amount of hybridization of a second sample to each polynucleotide probe in the plurality of polynucleotide probes, wherein: the first sample comprises molecules of a target polynucleotide having a target nucleotide sequence; and (b) the second sample comprises a plurality of different polynucleotide molecules, wherein each different polynucleotide molecule has a different nucleotide sequence.

The invention further provides, in yet other embodiments, a method for evaluating hybridization conditions of one or more polynucleotide probes, each of said one or more polynucleotide probes having a particular polynucleotide sequence. The method comprises comparing the amount of hybridization of a first sample to each of the one or more polynucleotide probes under particular hybridization conditions with the amount of hybridization of a second sample to each of the one or more polynucleotide probes under the same particular hybridization conditions. The first sample preferably comprises molecules of a target polynucleotide having a target nucleotide sequence. The second sample preferably comprises a plurality of different polynucleotide molecules wherein each different polynucleotide molecule has a different nucleotide sequence.

4. BRIEF DESCRIPTION OF THE DRAWINGS

FIG. 2A is the fluorescence intensity from a sample of 2 μg fragmented cRNA from yer019 w/- homozygous disruption yeast labeled with Cy3 ("green channel");

FIG. 2B is the fluorescence intensity from a sample of 1.6 ng fragmented pure YER019W labeled with Cy5 ("red channel").

FIG. 3A is the fluorescence intensity from a sample of 1.6 ng fragmented pure YER019W labeled with CY3 ("green channel");

FIG. 3B is the fluorescence intensity from a sample of 2 μg fragmented cRNA from yer019 w/- homozygous disruption yeast labeled with Cy5 ("red channel").

FIG. 4A is the fluorescence intensity from a sample of 2 μg fragmented cRNA from yer019w/- homozygous disruption yeast, labeled with Cy3 ("green channel");

FIG. 4B is the fluorescence intensity from a sample of 2 μg fragmented cRNA from wild-type yeast, labeled with Cy5 ("red channel").

Figures 2A, 2B:
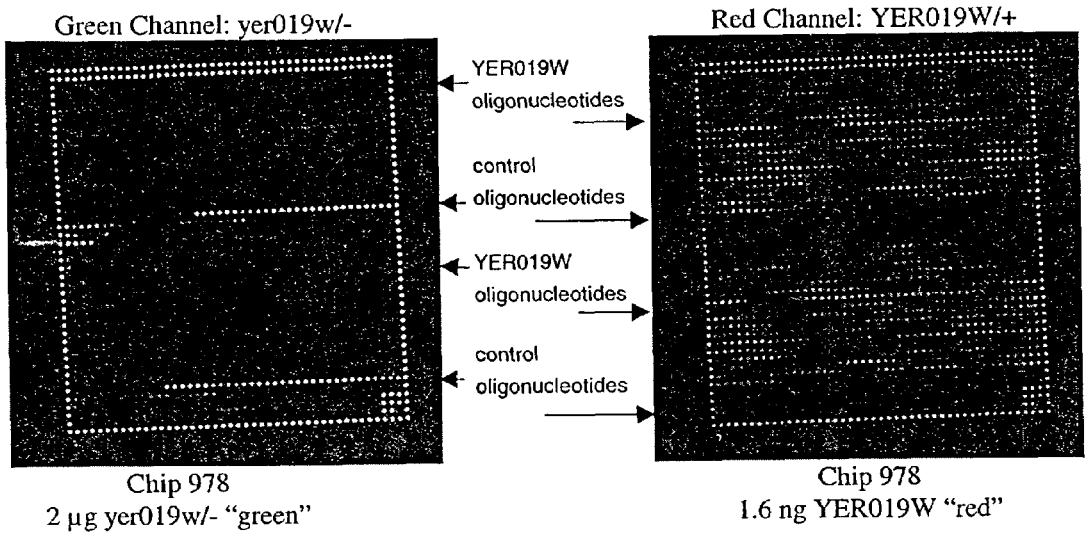
FIGS. 2A-2B show fluorescence intensity images from the simultaneous hybridization of two samples to a microarray comprising oligonucleotide probes complementary to the gene YER019W of the yeast *Saccharomyces cerevisiae* and control oligonucleotide probes as indicated.
Figures 3A, 3B:
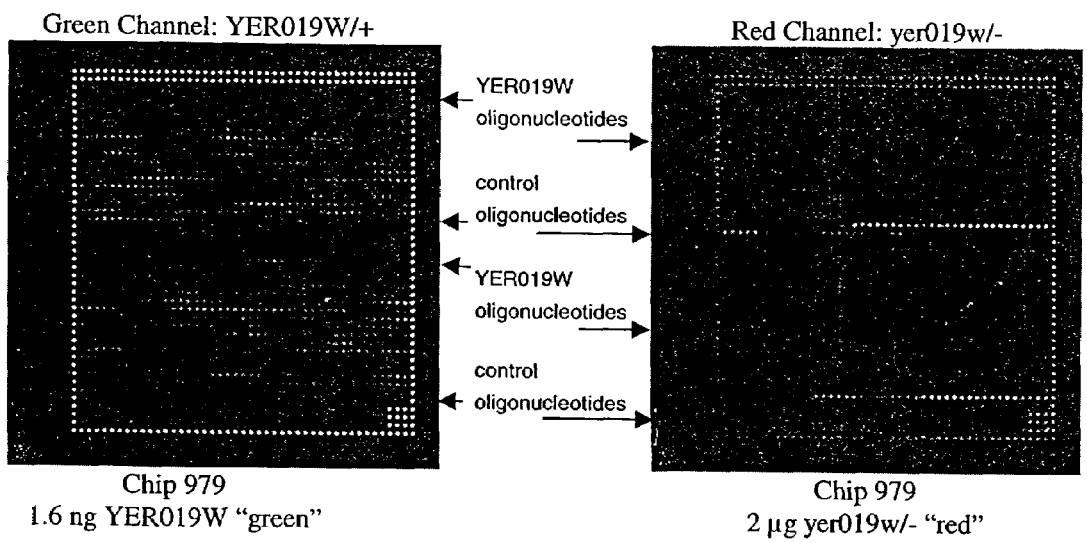
FIGS. 3A-3B show fluorescence intensity images from the simultaneous hybridization of two samples to a microarray identical to the array in FIGS. 2A-2B.
Figure 5A:
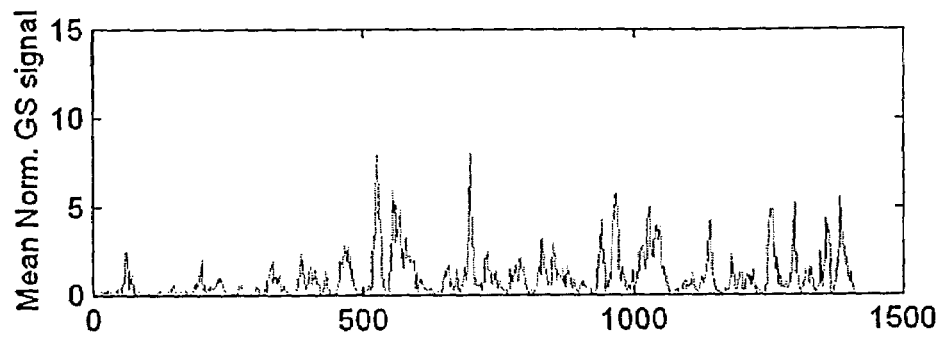
Figure 5B:
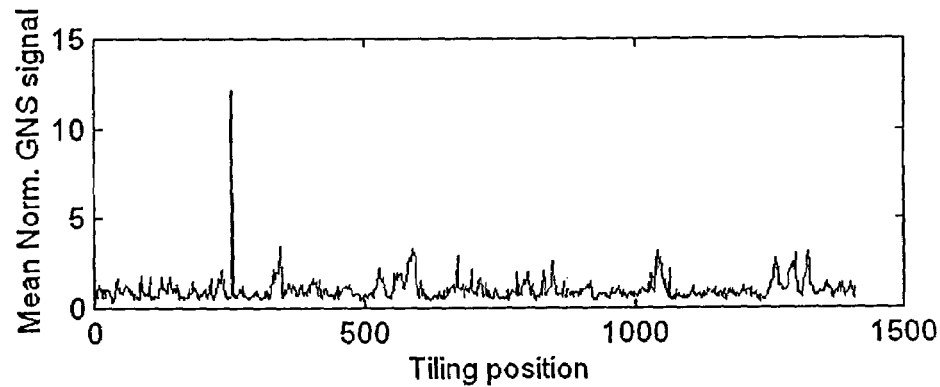
Figure 5C:
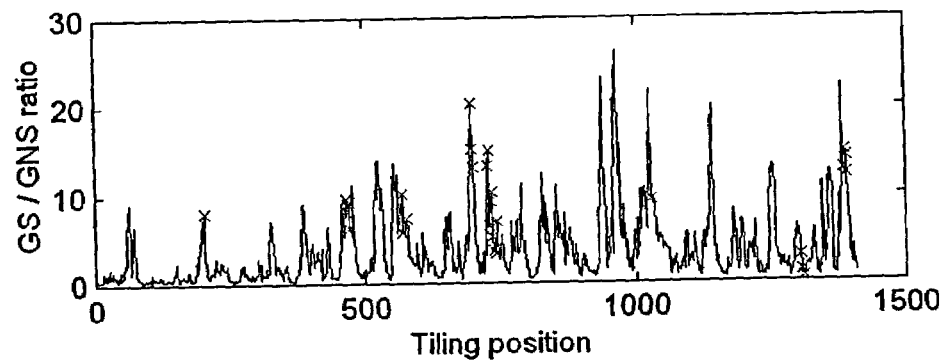

FIGS. 5A-C plots the amount of target and non-target hybridization observed for individual probes according to their "tiling positions." FIG. 5A plots the mean normalized hybridization intensity from the combined signal of labeled YER019W hybridization in FIGS. 2B and 3A; FIG. 5B plots the mean normalized hybridization intensity from the combined signal of labeled yer019w/- fragmented cRNA hybridization in FIGS. 2A and 3B; FIG. 5C plots the ratio of the targeted to non-targeted hybridization intensities plotted in FIGS. 5A and 5B, respectively.

Figure 6:
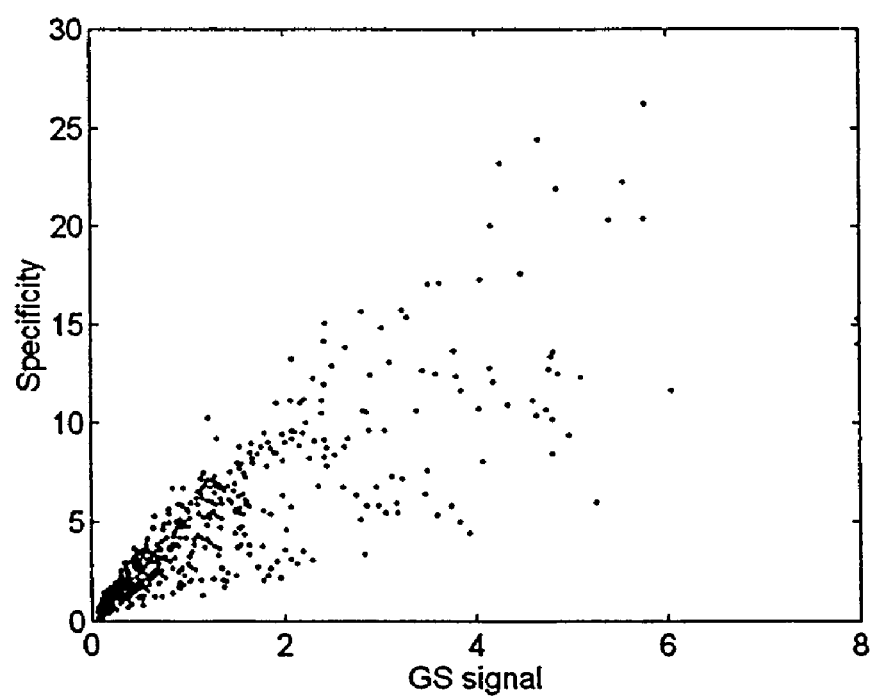

FIG. 6 is a scatter plot that diagrams relationships between sensitivity ("GS signal," horizontal axis) and specificity ("GNS signal," vertical axis) for each complementary probe of YER019W using the data in FIGS. 5A and 5C, respectively.

Figure 7:
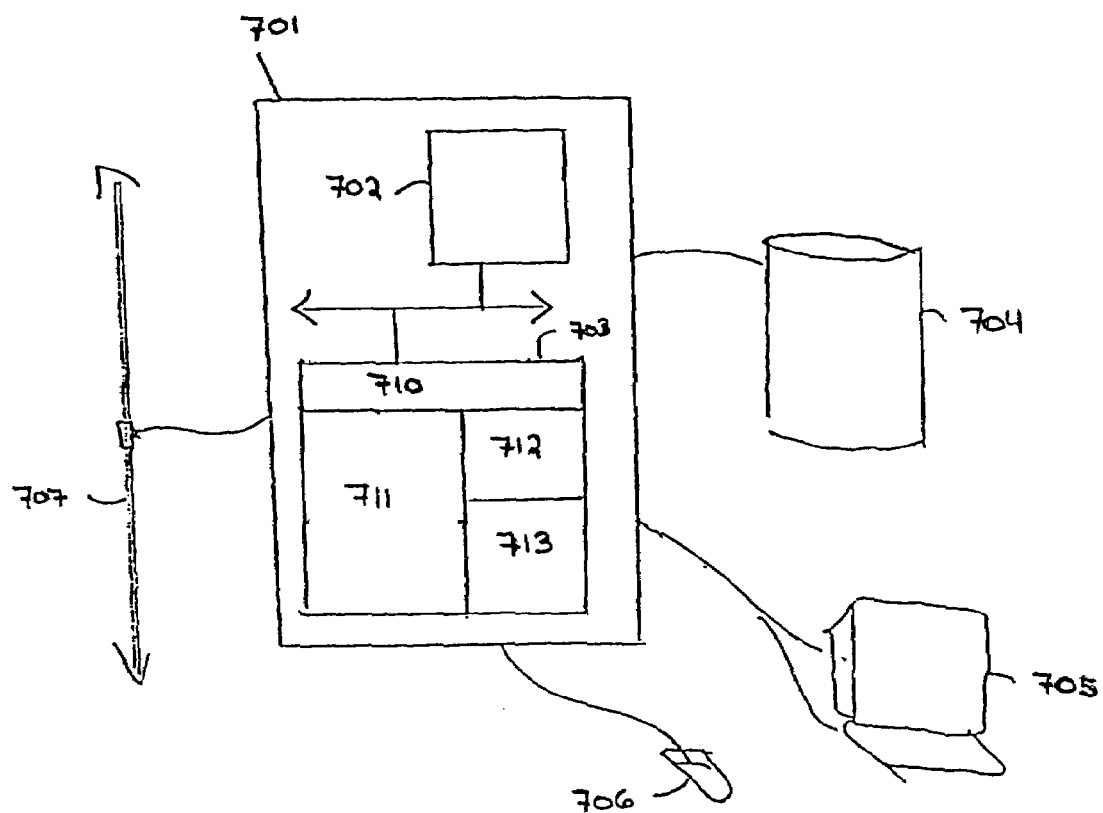

FIG. 7 is a representation of a computer system which may be used to practice the analytical methods of the present invention.

5. DETAILED DESCRIPTION

This section presents a detailed description of the present invention and its applications. The description is by way of several exemplary illustrations, in increasing detail and specificity, of the general methods of the invention. These examples are non-limiting, and related variants that will be apparent to one of skill in the art are intended to be encompassed by the appended claims.

In particular, the invention relates to methods and compositions that can be used to evaluate the properties of different probe molecules and, specifically, to evaluate both the sensitivity and the specificity with which a probe binds to a particular target. In particularly preferred embodiments, both the probe molecules and the target molecules are polynucleotides. Accordingly, the methods and compositions of the invention are described hereinbelow predominantly in terms of these embodiments (i.e., in terms of probes and targets that are polynucleotide molecules).

One skilled in the art can readily appreciate other embodiments, however, in which the methods and compositions of the invention are used to evaluate different types of probe molecules and target molecules. Indeed, the invention is equally applicable to any type of probe molecule and target molecule, although the probe molecules and target molecules are preferably of a type or class of molecules that can specifically bind to one another. For example, one skilled in the art can readily appreciate that in certain, alternative embodiments the probes of the invention can comprise antibodies (preferably monoclonal antibodies) while the target molecules can be any type of molecule to which an antibody can specifically bind. For example, the target molecules of the invention can also be protein or peptide molecules. One skilled in the art can also appreciate other alternative embodiments, and can make and use such alternative embodiments without undue experimentation. It is therefore understood that such alternative embodiments are also to be encompassed by the appended claims.

Section 5.1 first provides an introductory overview of the invention and, in particular, presents and defines certain concepts of the invention such as the concept of a probe and a target. A detailed description of the particular methods and compositions of the invention is then presented in Section 5.2. Specifically, this overview includes a description of the methods by which candidate probes are selected and prepared for evaluation (Subsection 5.2.1), a description of the hybridization samples used in the methods of the invention (Subsection 5.2.2), and a description of how hybridization levels can be measured for each of the two samples (Subsection 5.2.3). Subsection 5.2.4 also describes methods by which such hybridization data may be analyzed, e.g., to evaluate one or more probes and to determine the sensitivity and/or specificity of one or more probes.

The methods and compositions of the invention have many useful applications, e.g., in the selection and preparation of probes for microarrays. A few of these applications are presented in Section 5.3 below. Finally, an exemplary illustration of the methods and compositions of the invention is also provided below in Section 6. Specifically, this example demonstrates one particular and non-limiting embodiment of the invention wherein the methods and compositions of the invention are used to evaluate candidate probes for the gene YER019W of the yeast *Saccharomyces cerevisiae*.

5.1. Introduction

The present invention provides methods and compositions that can be used to evaluate binding properties of molecules of a given type, which are referred to herein as probe molecules, to molecules of a second type, which are referred to herein as target molecules. A probe or probe molecule, as the term is used herein, is understood to be any molecule that can be used to detect another molecule. Likewise, a target or target molecule, as the term is used herein, is understood to be any molecule that can be detected by using a probe.

Generally, a target molecule is detected by detecting the binding of the target molecule to a probe molecule. For example, in preferred embodiments probe molecules are immobilized on a solid (or, in certain embodiments a semi-solid) support or surface. A sample is then contacted to the solid support or surface under conditions such that target molecules that are intended to be detected by the probe molecules can bind thereto. The support or surface is subsequently washed under conditions such that molecules that are not bound to the probe molecules are removed, while the probe molecules and target molecules bound thereto remain. Preferably, the molecules in the sample are detectably labeled, e.g., with a fluorescent label or dye. Thus, binding of the target molecules to the probe molecules can be detected, e.g., by detecting the detectable label.

Preferably, molecules of a particular probe specifically detect a particular target. For example, in preferred embodiments wherein the probe molecules and the target molecules are polynucleotide molecules, the molecules of a particular probe preferably detect polynucleotide molecules having a particular polynucleotide sequence; e.g., a nucleotide sequence that is complementary to the nucleotide sequence of the probe molecules. Further, the polynucleotide sequence to be detected is frequently one sequence among hundreds or even thousands or hundreds of thousands in a particular sample. Thus, in order for a probe to specifically detect a particular target, it is generally preferably that the probe bind specifically to that target. Specifically, it is generally preferred that the specific binding of a particular target to a probe be maximized, while the non-specific binding of molecules to the probe is preferably minimized.

As noted above, probes and targets can comprise any type or class of molecule, although they are preferably of a type or class of molecule that specifically bind to each other. For example, antibodies are useful probes for detecting molecules such as proteins and peptides to which they specifically bind.

In particularly preferred embodiments of the invention, the probes and targets both comprise polynucleotide molecules. Specifically, polynucleotide molecules, which can generally be characterized by their nucleotide sequences, can bind or hybridize to other polynucleotide molecules by forming non-covalent Watson-Crick base pairs. Thus, target polynucleotide molecules having a particular nucleotide sequence can be readily detected by means of polynucleotide probe molecules having a complementary sequence.

"Target" polynucleotide, as the term is used herein, refers to molecules of a particular polynucleotide sequence of interest. Exemplary target polynucleotides which may be analyzed by the methods and compositions of the present invention include, but are not limited to DNA molecules such as genomic DNA molecules, cDNA molecules and fragments thereof, including oligonucleotides, expressed sequence tags ("ESTs"), sequence tag sites ("STSs"), etc. Target polynucleotides which may be analyzed by the methods and compositions of the invention also include RNA molecules such as, but by no means limited to messenger RNA (mRNA) molecules, ribosomal RNA (rRNA) molecules, cRNA (i.e., RNA molecules prepared from cDNA molecules that are transcribed in vivo) and fragments thereof.

The target polynucleotides may be from any source. For example, the target polynucleotide molecules may be naturally occurring nucleic acid molecules such as genomic or extragenomic DNA molecules isolated from a cell or organism, or RNA molecules, such as mRNA molecules, isolated from a cell or organism. Alternatively, the polynucleotide molecules may be synthesized, including, e.g., nucleic acid molecules synthesized enzymatically in vivo or in vitro, such as cDNA molecules, or polynucleotide molecules synthesized by PCR, RNA molecules synthesized by in vitro transcription, etc. The sample of target polynucleotides can comprise, e.g., molecules of DNA, RNA, or copolymers of DNA and RNA. In preferred embodiments, the target polynucleotides of the invention will correspond to particular genes or to particular gene transcripts (e.g., to particular mRNA sequences expressed in cells or to particular cDNA sequences derived from such mRNA sequences). However, in many embodiments, particularly those embodiments wherein the polynucleotide molecules are derived from mammalian cells, the target polynucleotides may correspond to particular fragments of a gene transcript. For example, the target polynucleotides may correspond to different exons of the same gene, e.g., so that different splice variants of that gene may be detected and/or analyzed.

Preferably, the polynucleotides analyzed by the compositions and methods of the invention are derived from a cell or organism. Specifically, the target polynucleotides are preferably derived from and correspond to particular genes or gene transcripts (e.g., mRNA sequences or cDNA sequences derived therefrom) of a cell or organism. The probes evaluated using the methods and compositions of the invention are therefore preferably intended for the detection of particular gene and gene transcripts, e.g., in samples of polynucleotide molecules derived from, and therefore expressed by, a cell or organism.

Cells and organisms that can be manipulated by means of routine techniques, e.g., of in vitro homologous recombination and/or sexual genetics are particularly preferred. More specifically, preferred cells or organism include those cells or organisms for which specific deletion strains or mutants (e.g., strains in which one or more particular genes or interest are deleted) are readily available. Such cells and organism include bacterial cells and organisms such as *Escherichia coli*, and yeast cells and organisms such as *Saccharomyces cerevisiae* to name a few. Other cells and organisms for which specific deletion strains or mutants can be readily obtained without undue experimentation will also be apparent to those skilled in the art.

It is understood, however, that the methods and compositions of the invention can be used to evaluate probes for polynucleotides from any cell or organism, including cells form higher organisms, e.g., plant cells and animal cells including mammalian cells such as cells from a mouse, a rat, or a human organism to name a few. The methods and compositions of the invention can be used to evaluate probes for polynucleotides from an organism even though specific deletion strains or mutants may not be available.

Although, for simplicity, this disclosure often makes reference to single cells (e.g., "RNA is isolated from a cell"), it is understood that more often any particular step of the invention will be carried out using a plurality of genetically and transcriptionally identical cells, e.g., from a cultured cell line. Such similar cells are also referred to herein as a "cell type." Cells of a particular cell type can be either from naturally single celled organisms such as yeast or bacteria, or can be derived from multi-cellular higher organisms. It is also understood, however, that the methods of the invention can be practiced using samples (e.g., mRNA samples) that are extracted from a plurality of cells, e.g., in a tissue sample from an organism such as a patient. Cells in such samples will, in general, still be genetically identical, but they will typically comprise different cell types of an organism that express at least some different genes. In other instances, however, the cells may be cells, such as cancer cells, that contain one or more genetic mutations and are not, therefore, genetically identical.

In preferred embodiments, the target polynucleotides to be analyzed are prepared in vitro from nucleic acids extracted from cells. For example, in one embodiment, RNA is extracted from cells (e.g., total cellular RNA) and messenger RNA is purified from the total extracted RNA. cDNA is then synthesized from the purified mRNA using, e.g., oligo-dT or random primers. Preferably, the target polynucleotides are short and/or fragmented polynucleotide molecules which are representative of the original nucleic acid population of the cell.

The target polynucleotides to be analyzed by the methods and compositions of the invention are preferably detectably labeled. For example, cDNA can be labeled directly, e.g., with nucleotide analogs, or indirectly, e.g., by making a second, labeled cDNA strand using the first strand as a template. Alternatively, the double-stranded cDNA can be transcribed into cRNA and labeled.

Preferably, the detectable label is a fluorescent label, e.g., by incorporation of nucleotide analogs. Other labels suitable for use in the present invention include, but are not limited to, biotin, iminobiotin, antigens, cofactors, dinitrophenol, lipoic acid, olefinic compounds, detectable polypeptides, electron rich molecules, enzymes capable of generating a detectable signal by action upon a substrate, and radioactive isotopes. Preferred radioactive isotopes include, $^{32}P$, $^{35}S$, $^{14}C$, $^{15}N$ and $^{125}I$, to name a few. Fluorescent molecules suitable for the present invention include, but are not limited to, fluorescein and its derivatives, rhodamine and its derivatives, texas red, 5'-carboxy-fluorescein ("FMA"), 2',7'-dimethoxy-4',5'-dichloro-6-carboxy-fluorescein ("JOE"), N,N,N',N'-tetramethyl-6-carboxy-rhodamine ("TAMRA"), 6'-carboxy-X-rhodamine ("ROX"), HEX, TET, IRD40 and IRD41. Fluorescent molecules that are suitable for the invention further include: cyamine dyes, including but not limited to Cy2, Cy3, Cy3.5, Cy5, Cy5.5, Cy7 and FluorX; BODIPY dyes, including but not limited to BODIPY-FL, BODIPY-TR, BODIPY-TMR, BODIPY-630/650, and BODIPY-650/670; and ALEXA dyes, including but not limited to ALEXA-488, ALEXA-532, ALEXA-546, ALEXA-568, and ALEXA-594; as well as other fluorescent dyes known to those skilled in the art. Electron rich indicator molecules suitable for the present invention include, but are not limited to, aferritin, hemocyanin, and colloidal gold. Alternatively, in less preferred embodiments the target polynucleotides may be labeled by specifically complexing a first group to the polynucleotide. A second group, covalently linked to an indicator molecule and which has an affinity for the first group, can be used to indirectly detect the target polynucleotide. In such an embodiment, compounds suitable for use as a first group include, but are not limited to, biotin and iminobiotin.

The target polynucleotides which are analyzed (e.g., detected) by the methods and compositions of the invention are contacted to a probe or to a plurality of probes under conditions such that polynucleotide molecules having sequences complementary to the probe hybridize thereto. As used herein, a "probe" refers to polynucleotide molecules of a particular sequence to which target polynucleotide molecules having a particular sequence (generally a sequence complementary to the probe sequence) are capable of hybridizing so that hybridization of the target polynucleotide molecules to the probe can be detected. The polynucleotide sequences of the probes may be, e.g., DNA sequences, RNA sequences or sequences of a copolymer of DNA and RNA. For example, the polynucleotide sequences of the probes may be full or partial sequences of genomic DNA, cDNA, mRNA or cRNA sequences extracted from cells. The polynucleotide sequences of the probes may also be synthesized, e.g., by oligonucleotide synthesis techniques known to those skilled in the art. The probe sequences can also be synthesized enzymatically in vivo, enzymatically in vitro (e.g., by PCR) or non-enzymatically in vitro.

Preferably, the probes used in the methods of the present invention are immobilized to a solid support or surface such that polynucleotide sequences that are not hybridized or bound to the probe or probes may be washed off and removed without removing the probe or probes and any polynucleotide sequence bound or hybridized thereto. In one particular embodiment, the probes will comprise an array of distinct polynucleotide sequences bound to a solid (or semi-solid) support or surface such as a glass surface. Most preferably, the array is an addressable array wherein each different probe is located at a specific known location on the support or surface such that the identity of a particular probe can be determined from its location on the support or surface.

Although the probes used in the invention can comprise any type of polynucleotide, in preferred embodiments the probes comprise oligonucleotide sequences (i.e., polynucleotide sequences that are between about 4 and about 200 bases in length, and are more preferably between about 15 and about 150 bases in length). In one embodiment, shorter oligonucleotide sequences are used that are between about 4 and about 40 bases in length, and are more preferably between about 15 and about 30 bases in length. However, a more preferred embodiment of the invention uses longer oligonucleotide probes that are between about 40 and about 80 bases in length, with oligonucleotide sequences between about 50 and about 70 bases in length (e.g., oligonucleotide sequences of about 60 bases in length) being particularly preferred.

The invention is based, at least in part, on the discovery the nonspecific hybridization to a particular probe may be assayed by supplying a distinguishable hybridization sample of competing molecules. In particular, non-specific hybridization samples can be readily obtained which comprise polynucleotide sequences other than the particular sequences intended to specifically hybridize to a probe. Rather, the polynucleotide sequences of such non-specific hybridization samples are competing polynucleotides of the same type and having the same abundances as competing polynucleotides in experimental samples for which the probe is intended.

5.2. Overview of the Methods of the Invention

Figure 1:
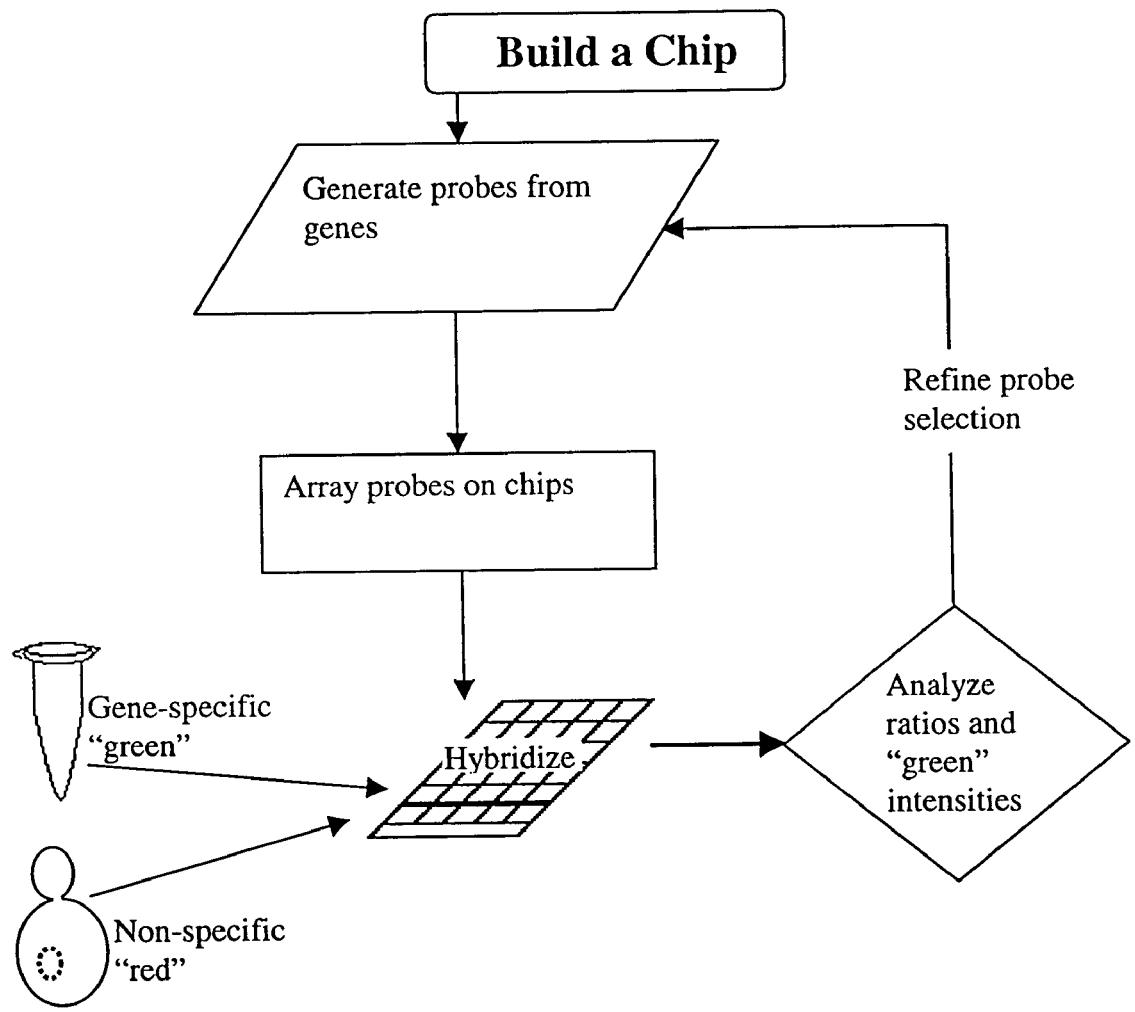
FIG. 1 shows a flow chart illustrating an exemplary embodiment of the invention wherein the methods are used to evaluate oligonucleotide probes on a microarray.

A flow chart illustrating an exemplary, non-limiting embodiment of the invention is shown in FIG. 1. This particular embodiment evaluates the hybridization properties of a plurality of different polynucleotide probes on a microarray and, more specifically, can be used to evaluate the sensitivity and/or specificity with which each of the different probes hybridizes to a particular target polynucleotide.

In the particular embodiment depicted in FIG. 1, a microarray or "chip" of polynucleotide probes is designed and built by first selecting a plurality of different oligonucleotide sequences (101) to evaluate by the methods of the invention, followed by synthesis of a microarray of the selected oligonucleotide sequences (102), e.g., by ink jet synthesis technology.

Two, differentially labeled hybridization samples are also prepared: a specific hybridization sample (103) and a non-specific hybridization sample (104). For example, in the particular embodiment shown in FIG. 1 the specific hybridization sample (103) is a "gene specific" sample comprising the purified target polynucleotide (e.g., polynucleotide molecules of a purified gene of interest) labeled with a green fluorescent label (e.g., a fluorophore such as Cy3 that fluoresces green light when stimulated). The exemplary non-specific hybridization sample (104) comprises a sample of polynucleotides from a "deletion strain" of the cell or organism (i.e., from a strain of a cell or organism that does not express the target polynucleotide) labeled with a red fluorescent label (e.g., a fluorophore such as Cy5 that fluoresces red light when stimulated). Thus, the non-specific hybridization sample is a polynucleotide sample wherein the target polynucleotide has been removed or deleted.

Both the specific and the non-specific hybridization samples are hybridized to the probes (105), preferably simultaneously, and the intensity of their respective labels is measured. The signal intensities and/or ratios are then analyzed (106) and used to evaluate the hybridization properties of the different probes.

Each of the steps depicted in FIG. 1 is described in detail below with respect to general aspects of the invention and in terms of specific, exemplary embodiments. In particular, subsection 5.2.1, below, describes certain exemplary methods by which candidate probes can be selected for evaluation by the methods of the invention. In particularly preferred embodiments of the invention, the candidate probes comprise microarrays of probes. Accordingly, subsection 5.2.1 also describes and enables microarrays as well as methods for preparing the candidate probes for microarrays.

Subsection 5.2.2 describes and enables both the specific hybridization samples and the non-specific hybridization samples which are used in the invention to evaluate the candidate probes. The description includes a description of certain particularly preferred embodiments of both the specific hybridization samples and the non-specific hybridization samples which that can be used in the invention. Exemplary methods and compositions for labeling such samples are also described in Section 5.2.2, including the differential labeling methods that are preferred in the present invention. Subsection 5.2.3 describes methods of measuring hybridization of the two samples (i.e., the specific and non-specific hybridization samples) to the candidate probes, including descriptions of appropriate hybridization conditions. Finally, subsection 5.3 describes methods by which the hybridization data thus obtained can be analyzed, e.g., to evaluate the sensitivity and specificity of individual probes to the target polynucleotide.

5.2.1. Selection of Candidate Probes

In the exemplary method depicted in FIG. 1, one or more polynucleotide probes are provided or selected for analysis according to the methods of the invention. In particular, the polynucleotide probes that are analyzed according to the methods of the invention comprise a nucleotide sequence that is capable of hybridizing to molecules of a target polynucleotide under appropriate hybridization conditions. Generally, the target polynucleotide molecules that hybridize to a probe contain at least one nucleotide sequence that is complementary to the nucleotide sequence of the probe and can therefore hybridize to the probe by forming noncovalent Watson-Crick base pairs with the nucleotides of the probe sequence. Accordingly, polynucleotide probes can be selected or provided by selecting or providing polynucleotide probes having different nucleotide sequences. Because the preferred target polynucleotide molecules of the invention are polynucleotide molecules corresponding to genes or gene transcripts of a cell or organism, the selected or provided polynucleotide probes preferably have nucleotide sequences that are complementary to at least a portion of the nucleotide sequence of a gene or gene transcript of interest.

In preferred embodiments, the polynucleotide probes that are selected or provided for analysis are oligonucleotide probes; i.e., the probes comprise oligonucleotide sequences. Oligonucleotide sequences are short sequences of polynucleotides that are preferably between about 4 and about 200 bases (i.e., nucleotides) in length, and are more preferably between about 15 and about 150 bases in length. In one embodiment, shorter oligonucleotide sequences are used that are less than about 40 bases in length, and are preferably between about 15 and 30 bases in length. However, a preferred embodiment of the invention uses longer oligonucleotide sequences between about 40 and about 80 bases in length, with oligonucleotide sequences between about 50 and about 70 bases in length being preferred, and oligonucleotide sequences between about 50 and about 60 bases in length being even more preferred.

The compositions and methods of the invention can be used, in general, to evaluate the hybridization properties of any probe or probes comprising a polynucleotide sequence that are immobilized to a solid support or surface. For example, as described supra, the probes can comprise DNA sequences, RNA sequences, or copolymer sequences of DNA and RNA. The polynucleotide sequences of the probes can also comprise DNA and/or RNA analogs or combinations thereof. For example, the polynucleotide sequences of the probes can be full or partial sequences of genomic DNA, cDNA, mRNA or cRNA sequences extracted from cells. The polynucleotide sequences of the probes can also be synthesized nucleotide sequences, such as synthetic oligonucleotide sequences. The probe sequences can be synthesized either enzymatically in vivo, enzymatically in vitro (e.g., by PCR), or non-enzymatically in vitro.

The probe or probes used in the methods and compositions of the invention are preferably immobilized to a solid support which can be either porous or non-porous. For example, the probes can be polynucleotide sequences that are attached to a nitrocellulose or nylon membrane or filter. Such hybridization probes are well known in the art (see, e.g., Sambrook et al., eds., 1989, *Molecular Cloning: A Laboratory Manual*, 2nd Ed., Vols. 1-3, cold Spring Harbor Laboratory, Cold Spring Harbor, N.Y.). Alternatively, the solid support or surface can be a glass or plastic surface, or it can be a semi-solid support such as a gel.

Microarrays Generally:

In a particularly preferred embodiment, hybridization levels are measured to microarrays of probes consisting of a solid phase on the surface of which are immobilized a population of polynucleotides, such as a population of DNA or DNA mimics or, alternatively, a population of RNA or RNA mimics. The solid phase may be a nonporous or, optionally, a porous material such as a gel. Microarrays can be employed, e.g., for analyzing the transcriptional state of a cell such as the transcriptional states of cells exposed to graded levels of a drug of interest or to graded perturbations to a biological pathway of interest. Microarrays are particularly useful in the methods of the instant invention in that they can be used to simultaneously screen a plurality of different probes to evaluate, e.g., each probe's sensitivity and specificity for a particular target polynucleotide.

In preferred embodiments, a microarray comprises a support or surface with ordered array of binding (e.g., hybridizing) sites, e.g., for a plurality of different probes. Microarrays can be made in a number of ways, of which several are described hereinbelow. However produced, microarrays share certain characteristics: The arrays are reproducible, allowing multiple copies of a given array to be produced and easily compared with each other. Preferably, the microarrays are made from materials that are stable under binding (e.g., nucleic acid hybridization) conditions. The microarrays are preferably small, e.g., between about 5 $cm^2$ and 25 $cm^2$, preferably about 12 to 13 $cm^2$. However, larger arrays are also contemplated and may be preferable, e.g., for simultaneously evaluating a very large number of different probes.

Preferably, a given binding site or unique set of binding sites in the microarray will specifically bind (e.g., hybridize) to the product of a single gene or gene transcript from a cell or organism (e.g., to a specific mRNA or to a specific cDNA derived therefrom). However, as discussed above, in general other, related or similar sequences will cross hybridize to a given binding site.

The microarrays used in the methods and compositions of the present invention include one or more test probes, each of which has a polynucleotide sequence that is complementary to a subsequence of RNA or DNA to be detected. Each probe preferably has a different nucleic acid sequence, and the position of each probe on the solid surface of the array is preferably known. Indeed, the microarrays are preferably addressable arrays, more preferably positionally addressable arrays. More specifically, each probe of the array is preferably located at a known, predetermined position on the solid support such that the identity (i.e., the sequence) of each probe can be determined from its position on the array (i.e., on the support or surface).

Preferably, the density of probes on a microarray is about 100 different (i.e., non-identical) probes per 1 $cm^2$ or higher. More preferably, a microarray used in the methods of the invention will have at least 550 probes per 1 $cm^2$, at least 1,000 probes per 1 $cm^2$, at least 1,500 probes per 1 $cm^2$ or at least 2,000 probes per 1 $cm^2$. In a particularly preferred embodiment, the microarray is a high density array, preferably having a density of at least about 2,500 different probes per 1 $cm^2$. The microarrays used in the invention therefore preferably contain at least 2,500, at least 5,000, at least 10,000, at least 15,000, at least 20,000, at least 25,000, at least 50,000 or at least 55,000 different (i.e., non-identical) probes.

In one embodiment, the microarray is an array (i.e., a matrix) in which each positions represents a discrete binding site for a product encoded by a gene (i.e., for an mRNA or for a cDNA derived therefrom). For example, the binding site can be a DNA or DNA analog to which a particular RNA can specifically hybridize. The DNA or DNA analog can be, e.g., a synthetic oligomer, a full length cDNA, a less than full length cDNA, or a gene fragment.

Preferably, the microarrays used in the invention have binding sites (i.e., probes) for one or more genes relevant to the action of a drug of interest or in a biological pathway of interest. A "gene" is identified as an open reading frame (ORF) that encodes a sequence of preferably at least 50, 75, or 99 amino acid residues from which a messenger RNA is transcribed in the organism or in some cell or cells of a multicellular organism. The number of genes in a genome can be estimated from the number of mRNAs expressed by the cell or organism, or by extrapolation of a well characterized portion of the genome. When the genome of the organism of interest has been sequenced, the number of ORFs can be determined and mRNA coding regions identified by analysis of the DNA sequence. For example, the genome of *Saccharomyces cerevisiae* has been completely sequenced and is reported to have approximately 6275 ORFs encoding sequences longer the 99 amino acid residues in length. Analysis of these ORFs indicates that there are 5,885 ORFs that are likely to encode protein products (Goffeau et al., 1996, *Science* 274:546-567). In contrast, the human genome is estimated to contain approximately $10^5$ genes.

Preparing Probes for microarrays:

As noted above, the "probe" to which a particular target polynucleotide molecule specifically hybridizes according to the invention is a complementary polynucleotide sequence to the target polynucleotide. In one embodiment, the probes of the microarray comprises sequences greater than 500 nucleotide bases in length that correspond to a gene or gene fragment. For example, such probes can comprise DNA or DNA "mimics" (e.g., derivatives and analogs) corresponding to at least a portion of one or more genes in an organism's genome. In another embodiment, such probes are complementary RNA or RNA mimics.

DNA mimics are polymers composed of subunits capable of specific, Watson-Crick-like hybridization with DNA, or of specific hybridization with RNA. For example, the DNA mimics can comprise nucleic acids modified at the base moiety, at the sugar moiety, or at the phosphate backbone. For example, one particular DNA mimic includes, but is not limited to, phosphorothioates.

Such DNA sequences can be obtained, e.g., by polymerase chain reaction (PCR) amplification of gene segments from, e.g., genomic DNA, mRNA (e.g., from RT-PCR) or from cloned sequences. PCR primers are preferably chosen based on known sequences of the genes or cDNA that result in amplification of unique fragments (i.e., fragments that do not share more than 10 bases of contiguous identical sequence with any other fragment on the microarray). Computer programs that are well known in the art are useful in the design of primers with the required specificity and optimal amplification properties, such as Oligo version 5.0 (National Biosciences). Typically, each probe on the microarray will be between about 20 bases and about 50,000 bases, and usually between about 300 bases and about 1,000 bases in length. PCR methods are well known in the art and are described, e.g., by Innis et al., eds., 1990, *PCR Protocols: A Guide to Methods and Applications*, Academic Press, Inc., San Diego, Calif. As will be apparent to one skilled in the art, controlled robotic systems are useful for isolating and amplifying nucleic acids.

An alternative, preferred means for generating the polynucleotide probes for a microarray used in the methods and compositions of the invention is by synthesis of synthetic polynucleotides or oligonucleotides, e.g., using N-phosphonate or phosphoramidite chemistries (Froehler et al., 1986, *Nucleic Acid Res.* 14:5399-5407; McBride et al., 1983, *Tetrahedron Lett.* 24:246-248). Synthetic sequences are typically between about 4 and about 500 bases in length, more typically between about 4 and about 200 bases in length, and even more preferably between about 15 and about 150 bases in length. In embodiments wherein shorter oligonucleotide probes are used, synthetic nucleic acid sequences less than about 40 bases in length are preferred, more preferably between about 15 and about 30 bases in length. In embodiments wherein longer oligonucleotide probes are used, synthetic nucleic acid sequences are preferably between about 40 and 80 bases in length, more preferably between about 40 and 70 bases in length and even more preferably between about 50 and 60 bases in length. In some embodiments, synthetic nucleic acids include non-natural bases, such as, but not limited to, inosine. As noted above, nucleic acid analogs may be used as binding sites for hybridization. An example of a suitable nucleic acid analog is peptide nucleic acid (see, e.g., Egholm et al., 1993, *Nature* 363:566-568; U.S. Pat. No. 5,539,083).

In other alternative embodiments, the hybridization sites (i.e., the probes) are made from plasmid or phage clones of genes, cDNAs (e.g., expressed sequence tags), or inserts therefrom (see, e.g., Nguyen et al., 1995, *Genomics* 29:207-209).

Attaching Probes to the Solid Surface:

The probes are preferably attached to a solid support or surface which may be made, e.g., from glass, plastic (e.g., polypropylene, nylon) polyacrylamide, nitrocellulose, a gel, or other porous or nonporous material. A preferred method for attaching the nucleic acids to the surface is by printing on glass plates, as is described generally by Schena et al., 1995, *Science* 270:467-470. This method is especially useful for preparing microarrays of cDNA (see also DeRisi et al., 1996, *Nature Genetics* 14:457-460; Shalon et al., 1996, *Genome Res.* 6:639-645; and Schena et al., 1995, *Proc. Natl. Acad. Sci. U.S.A.* 93:10539-11286).

Another preferred method for making microarrays is by making high-density oligonucleotide arrays. Techniques are known for producing arrays containing thousand of oligonucleotides complementary to defined sequences and at defined locations on a surface using photolithographic techniques for synthesis in situ (see Fodor et al., 1991, *Science* 251:767-773; Pease et al., 1994, *Proc. Natl. Acad. Sci. U.S.A.* 91:5022-5026; Lockhart et al., 1996, *Nature Biotechnology* 14:1675; U.S. Pat. Nos. 5,578,832; 5,556,752; and 5,510,270) or other methods for rapid synthesis and deposition of defined oligonucleotides (Blanchard et al., *Biosensors & Bioelectronics* 11:687-690). When these methods are used oligonucleotides (e.g., 25-mers) of known sequence are synthesized directly on a surface such as a derivatized glass slide. Usually, the array produced is redundant with several oligonucleotide molecules per RNA. Oligonucleotide probes can also be chosen to detect particular alternatively spliced mRNAs.

Other methods for making microarrays, e.g., by masking (Maskos and Southern, 1992, *Nucl. Acids. Res.* 20:1679-1684) can also be used. In principle and as noted above any type of array, for example dot blots on a nylon hybridization membrane (see Sambrook et al., supra) can be used. However, as will be recognized by those skilled in the art, very small arrays will frequently be preferred because hybridization volumes will be smaller.

In a particularly preferred embodiment, microarrays used in the invention are manufactured by means of an ink jet printing device for oligonucleotide synthesis, e.g., using the methods and systems described by Blanchard in International Patent Publication No. WO 98/41531, published on Sep. 24, 1998; Blanchard et al., 1996, *Biosensors and Bioeletronics* 11:687-690; Blanchard, 1998, in *Synthetic DNA Arrays in Genetic Engineering*, Vol. 20, J. K. Setlow, ed., Plenum Press, New York at pages 111-123. Specifically, the oligonucleotide probes in such microarrays are preferably synthesized by serially depositing individual nucleotides for each probe sequence in an array of "microdroplets" of a high tension solvent such as a propylene carbonate. The microdroplets have small volumes (e.g., 100 pL or less, more preferably 50 pL or less) and are separated from each other on the microarray (e.g., by hydrophobic domains) to form circular surface tension wells which define the locations of the array elements (i.e., the different probes).

Selecting Candidate Probes:

In one preferred embodiment, polynucleotide probes having a nucleotide sequence that is complementary to the nucleic acid sequence of a particular target polynucleotide are selected or provided by a method that is referred to herein as "tiling." Specifically, polynucleotide probes having a nucleotide sequence of length l are selected by selecting probes having a nucleotide sequence complementary to a sequence of l consecutive bases of the target polynucleotide sequence. For example, a polynucleotide probes can be selected or provided by selecting or providing a polynucleotide probe having a nucleotide sequence complementary to l consecutive bases of the target polynucleotide sequence beginning at the i'th base of the target polynucleotide sequence. In more detail, a first polynucleotide probe can be selected or provided by selecting or providing a polynucleotide probe whose polynucleotide sequence is complementary to the nucleotide sequence corresponding to bases i through i+l of the target polynucleotide sequence. A second polynucleotide probe sequence can be selected or provided by selecting or providing a polynucleotide probe whose nucleotide sequence is complementary to the nucleotide sequence corresponding to bases (i+n) through (i+n)+l of the target polynucleotide sequence, etc.

As noted supra, l specifies the length of the probe's polynucleotide sequence. Therefore, l is a positive integer, preferably having a value between about 4 and about 200, and more preferably having a value between about 15 and about 150. In embodiments wherein probes having shorter oligonucleotide sequences are used, l is preferably less than about 40, more preferably between about 15 and about 30. In embodiments wherein probes having longer oligonucleotide sequences are used, l is preferably between about 40 and about 80, more preferably between about 40 and about 70, more preferably between about 50 and about 60.

n, the "tiling interval," is a positive integer that preferably has a value between 1 and about 10. Particularly preferred values of the tiling interval include n=1, 2, 3, 4 and 5. i, which indicates the starting position within the target polynucleotide sequence, is also a positive integer. In certain preferred embodiments, the starting position is at or near the 5'-end of the target polynucleotide sequence. Thus, i has preferred values less than about 50, and more preferably less than about 10. The first base in the target polynucleotide sequence is a particularly preferred starting position in such embodiments. Accordingly, a particularly preferred value of the starting position is i=1. In other preferred embodiments, only the 3'-end of the target polynucleotide sequence is tiled. For example, in certain embodiments, only the last 2,000, more preferably the last 1,000, more preferably the last 500, and even more preferably the last 350 bases on the 3'-end of the target polynucleotide sequence are tiled. In such embodiments the value of the starting position i is adjusted accordingly (e.g., i=L−2,000; i=L−1,000; i=L−500; or i=L−350; wherein L is the length of the target polynucleotide sequence).

In certain embodiments, the probe or probes to be evaluated may be further selected, e.g., by selecting only probes that have or are predicted to have the highest binding (i.e., hybridization) energy $\Delta G$ to their target polynucleotide. Methods for calculating or predicting the hybridization energies of polynucleotide molecules are well known in the art and include, e.g., the nearest neighbor model (see, e.g., SantaLucia, 1998, *Proc. Natl. Acad. Sci. U.S.A.* 95:1460-1465). One skilled in the art can readily adapt such models to the different embodiments of the instant invention including, e.g., embodiments wherein the polynucleotide molecules are immobilized on the surface of a solid support such as in an array of polynucleotide probes (see, e.g., Provisional Patent Application Ser. No. 60/144,382, filed on Jul. 16, 1999; and U.S. patent application Ser. No. 09/364,751, filed on Jul. 30, 1999). Binding energies can be readily evaluated from such models, e.g., using mathematical algorithms and software such as those described, e.g., by Hyndman et al., 1996, *Biotechniques* 20:1090-1096.

In such embodiments, the binding energy can be calculated or predicted for each of a plurality of candidate probes for a target polynucleotide, such as for candidate probes selected by the above described tiling methods. Those probes predicted to have the highest binding energy are then selected for evaluation according to the methods of the present invention. Alternatively, those probes predicted to have a binding energy above a particular threshold (usually a threshold that is selected by a user) can be selected for evaluation according to the methods of the invention.

The above described methods are preferred methods for selecting polynucleotide probes regardless of the nature of the target polynucleotide sequence for which the probes are intended. In particular, the methods are preferred regardless of whether the target polynucleotide or target polynucleotides correspond to unique genes (e.g., for which no analog or homolog sequences are present or suspected of being present in a sample) or are members of one or more families of genes (e.g., for which one or more analogs or homologs are known and/or are expected to be present in a sample). The methods are also preferred regardless of the expected abundance of the target polynucleotides in a sample. Nevertheless, it will be understood by the skilled artisan that the methods and compositions of the present invention can be used to evaluate probes that are selected or provided by any method, and are not limited to embodiments wherein the probe or probe sequences are selected according to the tiling methods described hereinabove.

Although generally, the probes selected for evaluation according to the methods of the invention will be probes for only one particular target, it is understood that, at least in certain embodiments of the invention, probes for a plurality of different targets (e.g., for two or more different polynucleotide sequences) may be simultaneously selected and evaluated using the methods and compositions of the invention. For example, in one embodiment of the invention a Basic Local Alignment Search Tool ("BLAST") or PowerBLAST algorithm can be used to identify different polynucleotide sequences (e.g., among a database of expressed sequences such as the GenBank or dbEST database) that do not contain sequences that are expected or predicted cross-hybridize with each other's probes. Such polynucleotide sequences are referred to herein as "orthogonal" sequences or, in embodiments wherein the polynucleotide sequences are sequences of particular genes, as "orthogonal genes." Different probes that each hybridize to different orthogonal sequences can be analyzed simultaneously according to the methods of the present invention with minimal artifacts due to cross-hybridization by the gene-specific samples.

Algorithms for comparing polynucleotide sequences, such as the BLAST and PowerBLAST algorithms, are well known in the art (see, e.g., Altschul et al., 1990, *J. Mol. Biol.* 215:403-410; Altschul, 1997, *Nucleic Acids Res.* 25:3389-3402; and Zhang and Madden, 1997, *Genome Res.* 7:649-656). One skilled in the relevant art(s) therefore readily appreciates how to use such algorithms to compare polynucleotide sequences, e.g., using standard parameters well known in the art.

5.2.2. Hybridization Samples

The methods and compositions of the invention evaluate the properties of one or more probes by comparing the amount or level of binding of a first sample, referred to herein as a specific binding sample, to each of the one or more probes with the amount or level of binding of a second sample, referred to herein as a non-specific binding sample, to each of the one or more probes. In particularly preferred embodiments, the methods and compositions of the invention evaluate the properties of one or more polynucleotide probes by comparing the amount or level of binding (i.e., hybridization) of a first sample, referred to herein as a specific hybridization sample, to each of the one or more polynucleotide probes with the amount or level of binding of a second sample, referred to herein as a non-specific hybridization sample, to each of the one or more polynucleotide probes.

The first sample (i.e., the specific hybridization sample) comprises molecules of a particular target polynucleotide which, generally, is the intended target polynucleotide of the probe or probes to be evaluated. Alternatively, in those embodiments of the invention wherein probes are evaluated for two or more different orthogonal target polynucleotide sequences, the specific hybridization sample is preferably a sample comprising the two or more different polynucleotide sequences. The target polynucleotide (or the two or more orthogonal target polynucleotides) is preferably present in the specific hybridization sample in an amount or abundance that is comparable to the amount or abundance of the target polynucleotide in a sample for which a probe evaluated by the methods of the invention is intended (i.e., in a "real" sample). For example, in preferred embodiments wherein the target polynucleotide corresponds to a gene or gene transcript expressed by a cell or organism, the target polynucleotide is preferably present in the specific hybridization sample in an amount or abundance that is comparable to the amount or abundance of the target polynucleotide expressed by the cell or organism.

Most preferably, the target polynucleotide(s) is(are) present in the specific hybridization sample in an amount or abundance that is equal to its amount or abundance in a real sample. However, in many embodiments, the amount or abundance of the target polynucleotide(s) in a real sample is not known or is only approximately known. Accordingly, in alternative embodiments the target polynucleotide can be present in the specific hybridization sample in an amount or abundance that is approximately equal to its amount or abundance in a real sample. For example, the target polynucleotide can be present in the specific hybridization sample in an amount or abundance that is of the same order of magnitude as its amount or abundance in a real sample.

Alternatively, the target polynucleotide can be present in the specific hybridization sample in an amount or abundance that is within a minimum and a maximum amount or abundance that might be expected for any one polynucleotide sequence in a real sample. For example, typically amounts or abundances of a polynucleotide sequence in a real sample (i.e., in a sample of polynucleotide molecules extracted from a cell or organism) can be as low as about 0.0001% or as high as about 3% of the poly A+ mRNA extraced from the cell or organism. More preferably, the amount or abundance can be as high as about 2%, more preferably about 1% of the poly A+ mRNA extracted from the cell or organism. The amount or abundance of the polynucleotide sequence is more preferably no lower than about 0.0003% of the poly A+ mRNA extracted from the cell or organism. Thus, for example, the target polynucleotide can be present in the specific hybridization sample in an amount or abundance that is equal to or approximately equal to the average or mean amount or abundance of polynucleotides in a real sample. For example, in embodiments wherein the target polynucleotide corresponds to a gene or gene transcript of a cell or organism, the abundance or amount of the target polynucleotide in the specific hybridization sample can be equal to or approximately equal to the mean or average abundance or amount of genes or gene transcripts expressed by the cell or organism. Typical values of the mean or average abundance or amount of genes or gene transcripts expressed by a cell or organism are known to those skilled in the art, and generally depend on the identity of the cell or organism from which the gene or gene transcript is derived. For example, typical preferred values may include approximately 0.04% of all polyA+ mRNA extracted from a cell or organism.

In other embodiments, although the exact amount or abundance of a target polynucleotide in a real sample may not be known, its qualitative abundance will be known. For example, in embodiments wherein the target polynucleotide corresponds to a gene or gene transcript of a cell or organism, such genes or gene transcripts are often characterized as being expressed at low levels or abundances, moderate levels or abundances, or at high levels or abundances. Accordingly, a target polynucleotide can be present in a specific hybridization sample in amounts or abundances typical of such qualitative abundances. One skilled in the art readily appreciates values for levels or abundances of genes or gene transcripts in a sample that correspond to each of the above described categories (i.e., low, moderate and high). Generally, such values will depend on the particular cell type or organism from which the gene or gene transcript is derived. For example, preferred values can be about 1% or more of all polyA+ mRNA extracted from a cell for high levels or abundances, between about 0.01% and 1% of all polyA+ mRNA extracted from a cell for moderate levels or abundances, and less than about 0.01% of all polyA+ mRNA extracted from a cell for low levels or abundances.

The second sample (i.e., the non-specific hybridization sample) preferably comprises a plurality of different polynucleotide molecules, each different polynucleotide molecule having a different polynucleotide sequence. In particular, in those embodiments of the invention wherein the sequence of the target polynucleotide is the sequence of a particular gene or gene transcript in a cell or organism, the nucleotide sequences of the polynucleotide molecules in the second, nonspecific hybridization sample preferably comprise sequences representing the other genes or gene transcripts of the cell or organism.

Many possible different embodiments of the specific and non-specific hybridization samples are possible. For example, in a first preferred embodiment, the specific hybridization sample is a substantially pure sample of molecules having a particular polynucleotide sequence. Preferably, these molecules are molecules of a particular gene or gene transcript (e.g., mRNA or cDNA) and, accordingly, have the sequence of that gene or gene transcript. The specific hybridization sample in this first embodiment should be at least 75% pure (i.e., no more than 25% of the polynucleotide sequences in the sample are different from the sequence of the particular target polynucleotide or target polynucleotides). Preferably, in this first embodiment the specific hybridization sample is at least 90% pure, more preferably at least 95% pure and even more preferably at least 99% pure.

It is understood that such specific hybridization samples can be readily prepared by one skilled in the art according to routine methods currently known in the art and without undue experimentation. For example, polynucleotide molecules corresponding to a particular gene or gene transcript can be obtained, e.g., by polymerase chain reaction (PCR) amplification of gene segments from genomic DNA, cDNA, mRNA (e.g., by RT-PCR) or cloned sequences. PCR primers are preferably chosen based on known sequences of the target polynucleotide (e.g., of the particular gene or its gene transcript) that result in amplification of unique fragments. As the term is used herein, such "unique fragments" are fragments of a polynucleotide sequence that do not share more than 10 bases of contiguous identical sequence with any other fragment in a PCR (or RT-PCR) sample. Computer programs that are well known in the art are useful and can be used in the design of primers with the required specificity and optimal amplification properties, such as Oligo version 5.0 (National Biosciences). PCR methods are well known in the art and are described, for example, in Innis et al., Eds., 1990, *PCR Protocols: A Guide to Methods and Applications*, Academic Press, Inc., San Diego, Calif. It will be apparent to one skilled in the art the controlled robotic systems are useful for isolating and amplifying nucleic acids, including target polynucleotides of interest to a user.

In alternative embodiments, the target polynucleotide in a specific hybridization sample can be prepared from plasmid or phage clones of genes, cDNAs (e.g., expressed sequence tags), or inserts therefrom (see, for example, Nguyen et al., 1995, *Genomics* 29:207-209).

In this first embodiment, the second hybridization sample (i.e., the non-specific hybridization sample) comprises a plurality of different polynucleotide molecules, each different polynucleotide molecule having a different nucleotide sequence. In particular, each of the nucleotide sequences of the polynucleotide molecule in the non-specific hybridization sample should be different from the nucleotide sequence of the target polynucleotide in the specific hybridization sample. For example, in embodiments wherein the sequence of the target polynucleotide is the sequence of a particular gene or gene transcript of a cell or organism, the nucleotide sequences of the polynucleotide molecules in the second, non-specific hybridization sample preferably comprise sequences representing the other genes or gene transcripts of the cell or organism.

Such sequences are also preferably present in the non-specific hybridization sample in substantially the same abundances or amounts as their abundances or amounts in a "real" sample for which the probe or probes are intends, e.g., in the cell or organism. In particular, the amount or abundance or each polynucleotide sequence in such a non-specific hybridization sample preferably differs from its amount or abundance in a real sample by no more than a factor of 100, more preferably by no more than a factor of 10, even more preferably by no more than a factor of 2, and even more preferably by no more than a factor of 1.5 (i.e., by no more than 50%). It is understood, however, that in certain instances the relative amounts or abundances of a few polynucleotide sequences (e.g., preferably no more than about 5%, more preferably no more than about 1%, more preferably no more than about 0.1% of the different polynucleotide sequences in a non-specific hybridization sample) may differ by more than the preferred amounts recited above, as is typically observed, e.g., in samples from mutant cells or organisms or in samples from cells or organisms exposed to one or more drugs. However, the mean abundances of different polynucleotide sequences in the non-specific hybridization sample preferably does not differ substantially from the mean abundance of different polynucleotide sequence in most typical "real" samples. More specifically, the mean abundances preferably change by no more than a factor of two, more preferably by no more than 50%, even more preferably by no more than 10% and most preferably by no more than 1%.

Most preferably, the cell or organism is a cell or organism, such as *E. coli* or the yeast *Saccharomyces cerevisiae*, that can be manipulated according to routine techniques, e.g., of in vitro homologous recombination and sexual genetics, that are currently known in the art. In such embodiments, the non-specific hybridization sample can be prepared, e.g., from deletion mutants of such cells or organisms wherein the gene corresponding to the target polynucleotide sequence has been deleted or is silent (i.e., is not expressed by those cells).

Such non-specific hybridization samples can also be prepared from cells and organisms, including mammalian cells and organisms (e.g., mouse, rat and human cells or organisms) for which facile techniques, e.g., of in vitro homologous recombination and sexual genetics are not readily available. For example, non-specific hybridization sample can also be prepared from, e.g., from obligate diploids, such as from cell cultures including cultures of mammalian cells (e.g., mouse, rat or human cells) for which strains deleted for a specific gene (specifically, the gene corresponding to the target polynucleotide) are or can be made available.

Methods of preparing polynucleotide samples from such deletion mutants are well known in the art. For example, methods for preparing total and poly(A)$^+$ from a cell or organism are well known in the art, and are described generally, e.g., in Sambrook et al., eds., 1989, *Molecular Cloning: A Laboratory Manual*, 2nd Ed., Cold Spring Harbor Laboratory Press, Cold Spring Harbor, N.Y. In one embodiment, RNA is extracted from cells of the various types of interest using guanidinium thiocyanate lysis followed by CsCl centrifugation (Chirgwin et al., 1979, *Biochemistry* 18:5294-5299). In an alternative embodiment, which is preferred for *S. cerevisiae*, RNA is extracted from cells using phenol and chloroform, as described in Ausubel et al. (Ausubel et al., eds., 1989, *Current Protocols in Molecular Biology*, Vol. III, Green Publishing Associates, Inc., John Wiley & Sons, Inc., New York at pp. 13.12.1-13.12.5). Poly(A)$^+$ RNA is selected by selection with oligo-dT cellulose.

In one embodiment, RNA can be fragmented by methods known in the art, such as by incubation with $ZnCl_2$, to generate fragments of RNA. In one embodiment, isolated mRNA can be converted to antisense RNA synthesized by in vitro transcription of double-stranded cDNA in the presence of labeled dNTPs (Lockhart et al., 1996, *Nature Biotechnology* 14:1675).

In other embodiments, the polynucleotide molecules of the non-specific hybridization sample comprise DNA molecules, such as fragmented genomic DNA, first strand cDNA which is reverse transcribed from mRNA, or PCR products of amplified mRNA or cDNA. Methods for preparing such samples are also well known in the art, and one skilled in the art will readily appreciate how to prepare such non-specific hybridization samples with undue experimentation.

Alternatively, in those embodiments wherein deletion mutants of the cell or organism are not readily available, non-specific hybridization samples can also be prepared from mixtures of polynucleotides from which the target polynucleotide has been removed. For example, non-specific hybridization samples can be prepared from a library or libraries of selected clones that do not contain a clone or clones corresponding to the target polynucleotide, or from which clones corresponding to the target polynucleotide have been removed. Non-specific hybridization samples can also be prepared, e.g., from DNA or mRNA samples prepared from cells, as described above, which have been subtractively hybridized with the gene or interest (i.e., the gene corresponding to the target polynucleotide) to remove it from the sample or, at least, to partially remove it from the sample by reducing its abundance.

In a second preferred embodiment of the invention, the specific hybridization sample is identical to the specific hybridization sample of the first preferred embodiment described above. However, the non-specific hybridization sample of this second embodiment is preferably derived from a source with a normal amount of the target polynucleotide in addition to a plurality of other polynucleotide sequences. For example, in those embodiments wherein the sequence of the target polynucleotide is the sequence of a particular gene or gene transcript of a cell or organism, the nucleotide sequences of the polynucleotide molecules in the second, non-specific hybridization sample preferably comprise sequences representing both the gene or gene transcript corresponding to the particular target polynucleotide and the other genes or gene transcripts of the cell or organism.

Such non-specific hybridization samples can be prepared from normal or "wild type" cells or organisms that express the gene or gene transcript corresponding to the target polynucleotide sequence, as well as other genes or gene transcripts, in normal amounts, using methods of extracting polynucleotides from cells or organisms that are well known in the art and are described above for the preparation of a non-specific hybridization sample in the first particularly preferred embodiment of the invention. Accordingly, this second embodiment is particularly preferred in those aspects of the invention wherein the target polynucleotide corresponds, e.g., to a gene or gene transcript of a cell or organism for which deletion mutants are not readily available. The level of non-specific hybridization can be evaluated from such a sample according to the below described methods of the present invention; e.g., by subtracting the hybridization signal obtained from the specific hybridization sample from the hybridization signal obtained from the non-specific hybridization sample.

In a third preferred embodiment of the invention, the specific hybridization sample may contain, not only the target polynucleotide sequence, but also other non-target polynucleotide sequences. For example, in those embodiments of the invention wherein the sequence of the target polynucleotide is the sequence of a particular gene or gene transcript of a cell or organism, the nucleotide sequences of the polynucleotide molecules in the first, specific hybridization sample may comprise polynucleotide sequences corresponding to both the target polynucleotide and to the other genes or gene transcripts of the cell or organism. Thus, in such a third embodiment, the specific hybridization sample is preferably identical to the non-specific hybridization sample described, above, for the second preferred embodiment of the invention. In particular, the specific hybridization sample in this third embodiment of the invention is most preferably a polynucleotide sample obtained from a normal or wild type cell or organism that expresses the gene or gene transcript of the target polynucleotide, as well as other genes or gene transcripts, at normal levels for the cell or organism.

The second or non-specific hybridization sample in this third preferred embodiment of the invention is preferably identical to the non-specific hybridization sample described, above, for the first preferred embodiment of the invention. In particular, the non-specific hybridization in this third preferred embodiment preferably comprises a plurality of different nucleotide molecules, with each different polynucleotide molecule having a different polynucleotide sequence and with each polynucleotide sequence in the non-specific hybridization sample being different from the polynucleotide sequence of the target polynucleotide. For example, in particularly preferred aspects of this third embodiment, the nonspecific hybridization sample is a polynucleotide sample obtained from a deletion mutant of the cell or organism wherein the gene corresponding to the target polynucleotide sequence has been deleted or is silent. Such an embodiment is particularly preferred, e.g., in applications wherein it is important to evaluate the probe specificity and/or sensitivity at the natural abundance of the target polynucleotide.

In a fourth preferred embodiment of the invention, both the specific hybridization sample and the non-specific hybridization sample contain: (a) polynucleotide molecules having the polynucleotide sequence of the target polynucleotide; and (b) a plurality of different polynucleotide molecules, with each different polynucleotide molecule having a different polynucleotide sequence that is also different from the sequence of the target polynucleotide. In this fourth embodiment, the amount or level of molecules of the target polynucleotide in the first or specific hybridization sample differs substantially from the amount or level of the molecules of the target polynucleotide in the second or non-specific hybridization sample. Specifically, the amount or level of molecules of the target polynucleotide preferably differs by at least a factor of two, and more preferably by at least a factor four, more preferably by at least a factor of eight, still more preferably by at least a factor of 20, and even more preferably by at least a factor of 100.

Preferably in this fourth embodiment, the different polynucleotide molecules (i.e., the polynucleotide molecules having sequences that are different from the target polynucleotide sequence) are substantially identical in both the specific and non-specific hybridization samples. In particular, each of the other "non-target" polynucleotide sequences is preferably present in substantially the same amount or abundance in both samples, and these amounts or abundances are preferably substantially the same as the amounts or abundances of the polynucleotide sequences in a "real" sample (e.g., in a sample of polynucleotides from the cell or organism). Specifically, the amount or abundance of each non-target polynucleotide molecule preferably differs by no more than a factor of 100 between the two hybridization samples, more preferably by no more than a factor of 10, even more preferably by no more than a factor of two, and still more preferably by no more than a factor of 1.5 (i.e., by no more than 50%). It is understood, however, that larger changes in the relative abundance of a few polynucleotide sequences (e.g., preferably no more than about 5%, more preferably no more than about 1%, more preferably no more than about 0.1% of the different polynucleotide sequences in a non-specific hybridization sample) may occur between the two hybridization samples and/or between the hybridization samples and a real sample, as will typically be seen in samples derived, e.g., from mutant cells or organisms or from cells or organisms treated with one or more drugs. However, the mean change in the abundance or amount of all non-target polynucleotide sequences is preferably no more than a factor of two, more preferably no more than 50%, even more preferably no more than 10%, and still more preferably no more than 1%.

The polynucleotide molecules of both the specific hybridization sample and the non-specific hybridization sample are preferably detectably labeled. Preferably, the detectable label is a fluorescent label, e.g., by incorporation of nucleotide analogs. Other labels suitable for use in the present invention include, but are not limited to, biotin, imminobiotin, antigens, cofactors, dinitrophenol, lipoic acid, olefinic compounds, detectable polypeptides, electron rich molecules, enzymes capable of generating a detectable signal by action upon a substrate, and radioactive isotopes. Preferred radioactive isotopes include, $^{32}P$, $^{35}S$, $^{14}C$, $^{15}N$ and $^{125}I$, to name a few. Fluorescent molecules suitable for the present invention include, but are not limited to, fluorescein and its derivatives, rhodamine and its derivatives, texas red, 5'-carboxy-fluorescein ("FMA"), 2',7'-dimethoxy-4',5'-dichloro-6-carboxy-fluorescein ("JOE"), N,N,N',N'-tetramethyl-6-carboxy-rhodamine ("TAMRA"), 6'-carboxy-X-rhodamine ("ROX"), HEX, TET, IRD40 and IRD41. Fluorescent molecules that are suitable for the invention further include: cyamine dyes, including but not limited to Cy2, Cy3, Cy3.5, Cy5, Cy5.5, Cy7 and Fluor X; BODIPY dyes, including but not limited to BODIPY-FL, BODIPY-TR, BODIPY-TMR, BODIPY-630/650, and BODIPY-650/670; and ALEXA dyes, including but not limited to ALEXA-488, ALEXA-532, ALEXA-546, ALEXA-568, and ALEXA-594; as well as other fluorescent dyes known to those skilled in the art. Electron rich indicator molecules suitable for the present invention include, but are not limited to, aferritin, hemocyanin, and colloidal gold. Alternatively, in less preferred embodiments the target polynucleotides may be labeled by specifically complexing a first group to the polynucleotide. A second group, covalently linked to an indicator molecule and which has an affinity for the first group, can be used to indirectly detect the target polynucleotide. In such an embodiment, compounds suitable for use as a first group include, but are not limited to, biotin and iminobiotin.

In particularly preferred embodiments, the two samples (i.e., the specific hybridization sample and the non-specific hybridization sample) are differentially labeled. Specifically, each sample is labeled with a different detectable label (e.g., with a different, distinct fluorophore) such that the two samples can be simultaneously detected and distinguished from each other by detecting each sample's respectively label. For example, in one embodiment, the specific hybridization sample can be labeled using fluorescein-labeled dNTP, which fluoresces green, while the non-specific hybridization sample can be labeled using rhodamine-labeled dNTP, which fluoresces red. Each sample can then be readily detected and distinguished from the other sample by detecting the characteristic green or red fluorescence of each sample's respective label.

Indeed, by using such differential labeling the two hybridization samples can be distinguished from each other and separately detected even when they have been mixed. Thus, the specific hybridization sample and the non-specific hybridization sample need not be kept separate from each other, but can be mixed and hybridize to the polynucleotide probe or probes simultaneously, e.g., on the same microarray and in the same experiment. It is therefore not a requirement of the present invention that the specific hybridization sample and the non-specific hybridization sample be physically separate samples. The two samples need only be distinguishable, e.g., by means of the differential labeling scheme described above. Alternatively, one skilled in the art can readily appreciate that, in such embodiments, the specific hybridization sample and the non-specific hybridization can be thought of as the same sample with two different, distinct (e.g., differentially labeled) components: a specific hybridization component (corresponding to the specific hybridization sample discussed above), and a non-specific hybridization component (corresponding to the non-specific hybridization sample discussed above).

5.2.3. Measuring Hybridization Levels

The properties of one or more probes are evaluated according to the methods and compositions of the present invention by comparing the amount or level of binding of the first, specific binding sample to the probe or probes with the amount or level of the second, non-specific binding sample to the probe or probes. In preferred embodiments wherein the probes and targets comprise polynucleotide molecules, the amount or level of hybridization of the first, specific hybridization sample to the polynucleotide probe or probes is compared with the amount or level of hybridization of the second, non-specific hybridization sample to the polynucleotide probe or probes. Accordingly, in the methods of the invention preferably include a step wherein hybridization levels of the specific hybridization sample and the non-specific hybridization sample to the polynucleotide probe or probes are obtained or provided, e.g., by contacting the two samples to the polynucleotide probe or probes under conditions such that polynucleotide molecules in the samples can bind or hybridize to molecules of the probe or probes, and measuring the amount of polynucleotides from each of the two samples that bind or hybridize to molecules of the probe or probes.

Hybridization Conditions:

The conditions under which the polynucleotides are contacted to the probe or probes are known in the art as the "hybridization conditions." Preferably, the hybridization conditions are optimized such that specific binding of polynucleotide molecules to the probe or probes (e.g., binding of polynucleotide molecules from the specific hybridization sample) is high while non-specific binding of polynucleotide molecules to the probe or probes (e.g., binding of polynucleotide molecules from the non-specific hybridization sample) is low. In some embodiments, however, the optimal hybridization conditions may not be known or may only be approximately known. For example, in certain embodiments the methods and compositions of the invention can be used to evaluate particular hybridization conditions, e.g., to determine whether the hybridization conditions are optimal. For example, one or more of the hybridization parameters (e.g., the temperature and/or the salt concentration) can be systematically varied, and the methods of the invention can be used to determine, e.g., the specificity and/or sensitivity of the probe or probes for each hybridization condition. Appropriate or preferred hybridization conditions are then identified as the hybridization conditions for which the sensitivity and/or specificity of the probe or probes are greatest.

In particular embodiments wherein the probe or probes comprise double-stranded DNA sequences, the probe or probes, or arrays containing such probes are preferably subjected to denaturing conditions to render the DNA single-stranded prior to contacting with the target polynucleotide molecules. Arrays containing single-stranded probe DNA (e.g., synthetic oligodeoxyribonucleic acids) may also need to be denatured prior to contacting with the target polynucleotide molecules, e.g., to remove hairpins or dimers which form due to self complementary sequences.

Optimal hybridization conditions will depend on the length (e.g., oligomer versus polynucleotide greater than 200 bases) and type (e.g., RNA or DNA) of probes and target nucleic acids. General parameters for specific (i.e., stringency) hybridization conditions for nucleic acids are described, e.g., in Sambrook et al., eds., 1989, *Molecular Cloning: A Laboratory Manual,* 2nd Ed., Cold Spring Harbor Laboratory Press, Cold Spring Harbor, N.Y. at pp. 9.47-9.51 and 11.55-11.61; and in Ausubel et al., 1987, *Current Protocols in Molecular Biology*, Greene Publishing and Wiley-Interscience, New York. In embodiments, wherein cDNA microarrays are used, typical hybridization conditions are hybridization in 5×SSC plus 0.2% SDS at 65° C. for four hours, followed by washes at 25° C. in low stingency wash buffer (1×SSC plus 0.2% SDS), followed by 10 minutes at 25° C. in higher stringency wash buffer (0.1×SSC plus 0.2% SDS) (Shena et al., 1996, *Proc. Natl. Acad. Sci. U.S.A.* 93:10614). Useful hybridization conditions are also provided, e.g., Tijessen, 1993, *Hybridization With Nucleic Acid Probes*, Elsevier Science Publishers; B. V. and Kricka, 1992, *Nonisotopic DNA Probe Techniques*, Academic Press, San Diego.

In preferred embodiments wherein oligonucleotide probes are used, preferred hybridization conditions can comprise hybridization at a temperature at or near the mean melting temperature of the probes (e.g., within 5° C. or, more preferably, within 2° C.) in 1 M NaCl, 50 mM MES buffer (pH 6.5), 0.5% sodium sarcosine and 32% formamide.

The melting temperature ($T_m$) of a target polynucleotide from a particular probe is known in the art as referring to the temperature at which one-half (i.e., 50%) of the target polynucleotide molecules in a sample are bound to molecules of the probe. As the term is used herein to describe and enable appropriate hybridization conditions, the melting temperature of a probe refers to the melting temperature at which one-half of the target polynucleotide molecules in a sample having a nucleotide sequence that is complementary to the nucleotide sequence of the probe are hybridized thereto. Methods for determining the melting temperature of a particular polynucleotide duplex are well known in the art and include, e.g., predicting the melting temperature using well known physical models adapted to experimental data (see, e.g., SantaLucia, 1998, *Proc. Natl. Acad. Sci. U.S.A.* 95:11460-11465 and the references cited therein). Mathematical algorithms and software for predicting melting temperatures using such models are readily available as described, e.g., by Hyndman et al., 1996, *Biotechniques* 20:1090-1096. Although the specific parameter used in such models are generally derived for polynucleotide duplexes in solution, appropriate parameters can readily be obtained to predict melting temperatures and other hybridization properties of target polynucleotides hybridizing to polynucleotide probes that are immobilized on a solid surface, e.g., in a microarray. Indeed, one skilled in the art will readily appreciate how to obtain parameters that are appropriate for the probes of a specific microarray, as described, e.g., by Stoughton et al., in U.S. Provisional Application Ser. No. 60/144,382 filed on Jul. 16, 1999 and U.S. patent application Ser. No. 09/364,751 filed on Jul. 30, 1999. The melting temperature of an RNA/DNA duplex approximately 25 base pairs in length in 1 M salt solution is typically between about 60° C. and about 70° C.

Signal Detection:

The hybridization conditions used in the methods of the invention, including the specific hybridization conditions described above, also include washing conditions. The wash conditions are preferably such that polynucleotide molecules that are not bound to the probe or probes are removed (e.g., from the microarray of probes) while the probes and polynucleotide molecules that are bound thereto remain. The amount of polynucleotides hybridized to each probe can then be measured or determined, e.g., by measuring or determining the amount of the a detectable label.

As noted above, preferably polynucleotides from the two different samples (i.e., from the specific hybridization sample and the non-specific hybridization sample) are hybridized to the probes simultaneously. For example, in preferred embodiments of the invention wherein a plurality of different probes on a microarray are evaluated, the two samples are simultaneously hybridized to the binding sites on the microarray. In such embodiments, the polynucleotide molecules from each of the two samples are differentially labeled so that they can be distinguished. For example, cDNA in a specific hybridization sample can be labeled using fluorescein-labeled dNTP and cDNA from a non-specific hybridization sample can be labeled using rhodamine-labeled dNTP. When the two cDNAs are mixed and hybridized to the microarray, the relative intensity of signal from each cDNA set is determined for each site on the array, and any relative difference in abundance of a particular mRNA is thereby detected.

In the example described above, cDNA from the specific hybridization sample will fluoresce green when the fluorophore (i.e., the fluorescein label) is stimulated, and the cDNA from the non-specific hybridization sample will fluoresce red. As a result, when a particular probe (e.g., on the microarray) hybridizes specifically to a particular target polynucleotide (i.e., the target polynucleotide of the specific hybridization sample) the binding site for that probe on the microarray will emit a wavelength characteristic of the fluorescein label (i.e., green). In contrast, when a probe on the microarray cross-hybridizes to other polynucleotides (i.e., from the non-specific hybridization sample) the binding site for the probe on the microarray will emit a wavelength characteristic of both labels. A probe that hybridizes more specifically to the target polynucleotide of the specific hybridization sample will fluoresce with a higher ratio of green to red fluorescence, whereas a probe that hybridizes less specifically to that target polynucleotide will fluoresce with a lower ratio of green to red fluorescence.

The use of such a two-color fluorescence labeling and detection scheme as been described, e.g., to define alterations in gene expression (see, e.g., Shena et al., 1995, *Science* 270:467-470). An advantage of using cDNA labeled with two different fluorophores is that a direct and internally controlled comparison of hybridization levels corresponding to both specific and non-specific hybridization can be made. Variations due to minor differences in experimental conditions (e.g., hybridization conditions) will not affect subsequent analysis. However, it is understood that the invention can also be practiced using two physically separate samples and comparing, for example, the absolute amount of cDNA or mRNA (or other polynucleotides) from a specific hybridization sample that hybridizes to a probe and the absolute amount of cDNA or mRNA from a non-specific hybridization sample that hybridizes to the same probe.

When fluorescently labeled targets are used, the fluorescence emission at each site of a microarray can be, preferably, detected by scanning confocal laser microscopy. In one embodiment, a separate scan, using the appropriate excitation line, is carried out for each of the two fluorophores used. Alternatively, a laser can be used that allows simultaneous specimen illumination at wavelengths specific to the two fluorophores and emissions from the two fluorophores can be analyzed simultaneously (see Shena et al., 1996, *Genome Res.* 6:639-645). In a preferred embodiment, the arrays are scanned with a laser fluorescent scanner with a computer controlled X-Y stage and a microscope objective. Sequential excitation of the two fluorophores is achieved with a multi-line, mixed gas laser, and the emitted light is split by wavelength and detected with two photomultiplier tubes. Such fluorescence laser scanning devices are described, e.g., in Schena et al., 1996, *Genome Res.* 6:639-645. Alternatively, the fiber-optic bundle described by Ferguson et al., 1996, *Nature Biotech.* 14:1681-1684, may be used to hybridization levels at a large number of binding sites simultaneously.

Signals are recorded and, in a preferred embodiment, analyzed by computer, e.g., using a 12 bit analog to digital board. In one embodiment, the scanned image is despeckled using a graphics program (e.g., Hijaak Graphics Suite) and then analyzed using an image gridding program that creates a spreadsheet of the average hybridization at each wavelength at each site. If necessary, an experimentally determined correction for "cross talk" (or overlap) between the channels for the two fluorophores may be made. For any particular hybridization site on the microarray, a ratio of the emission of the two fluorophores can be calculated. The ratio is independent of the absolute amount or level of hybridization of either sample, but is useful, as explained above, for determining the relative amounts of specific and cross-hybridization from the two samples.

5.2.4. Data Analysis

The methods and compositions of the present invention are useful for evaluating one or more probes and, more specifically, can be used to evaluate the sensitivity and/or specificity with which a probe or probes bind or hybridize to a particular target. The sensitivity of a probe, as the term is used herein, is understood to refer to the absolute amount or level of a particular target (i.e., the number of molecules of the particular target) that binds to the probe under particular binding conditions. The amount or level of a particular target that binds to a probe under particular binding conditions is also referred to herein as the amount or level of specific binding to the probe under the particular binding conditions. In preferred embodiments of the invention wherein the probes and targets are polynucleotide molecules, the sensitivity of a probe (i.e., of a polynucleotide probe) is understood to refer to the absolute amount of a particular target polynucleotide (i.e., the number of polynucleotide molecules having a nucleotide sequence) that hybridizes to the polynucleotide probe under particular hybridization conditions. The amount of a particular target polynucleotide that hybridizes to a probe under particular hybridization conditions is also referred to herein as the amount of specific hybridization of the probe under the particular hybridization conditions.

The specificity of a probe, as the term is used herein, is understood to refer to the amount or level of a particular target (i.e., the number of molecules of the particular target) that binds to the probe under particular binding conditions relative to the amount or level of non-specific binding to the probe under the same binding conditions. Non-specific binding, as the term is used herein, is understood to refer to the amount of molecules other than molecules of the particular target (i.e., the number of molecules that are not molecules of the particular target) that bind to the probe under particular binding conditions. In preferred embodiments of the invention wherein the probes and targets are polynucleotide molecules, the sensitivity of a probe is understood to refer to the amount of a particular target polynucleotide (i.e., the number of polynucleotide molecules having a particular nucleotide sequence) that hybridizes to the probe under particular hybridization conditions compared to or relative to the amount of cross-hybridization to the probe under the same hybridization conditions. Cross-hybridization or non-specific hybridization, as the terms are used in preferred embodiments of the invention, are understood to refer to the amount of polynucleotides other than the particular target polynucleotide (i.e., the number of polynucleotide molecules having nucleotide sequences different that the nucleotide sequence of the particular target polynucleotide) that hybridize to the probe under particular hybridization conditions.

In the methods and compositions of the present invention, the specific hybridization T of a target polynucleotide to the probe p is directly related to the intensity I of the hybridization signal from the specific hybridization sample. This relationship can be readily expressed, e.g., by the equation:

$$T_p = s \cdot I_p^S \quad \text{(Equation 1)}$$

wherein $I_p^S$ is the intensity of the hybridization signal at probe p for the specific hybridization sample (i.e., the sample comprising the target polynucleotide sequence). s denotes a correction factor, e.g., for detector and label efficiencies.

Likewise, the amount of cross-hybridization X to the probe p is directly related to the intensity of the hybridization signal from the non-specific hybridization sample; i.e., by:

$$X_p = s \cdot I_p^{NS} \quad \text{(Equation 2)}$$

wherein $I_p^{NS}$ is the intensity of the hybridization signal at probe p for the non-specific hybridization sample (i.e., the sample deleted for the target polynucleotide).

One skilled in the art can therefore readily appreciate that by comparing the hybridization intensities $I_p^S$ and $I_p^{NS}$ from the two samples the sensitivity and specificity of a particular probe can be readily determined. In particularly preferred embodiments, such a comparison includes determining or obtaining the ratio of the hybridization intensity from the specific hybridization sample to the hybridization from the non-specific hybridization sample (i.e., the ratio $I_p^S/I_p^{NS}$). Specifically, as noted above the specificity of a probe is can be defined to be the amount of a particular target that binds or hybridizes to the probe under particular conditions relative to the amount of non-specific binding or hybridization to that probe under the same conditions. Thus, in one embodiment, the specificity S of the probe p is provided by the equation $$S_p = \frac{T_p}{X_p} \quad \text{(Equation 3)}$$

However, from Equations 1 and 2 above, it is readily apparent to one skilled in the art that the specificity can also be obtained or provided by the equation $$S_p = \frac{I_p^S}{I_p^{NS}} \quad \text{(Equation 4)}$$

Thus, the ratio of the hybridization intensities of the specific and non-specific hybridization samples provide a measure or value for the specificity of the probe.

Likewise, in the methods and compositions of the present invention the sensitivity of a probe p is determined or provided from the hybridization intensity of the specific hybridization sample to that probe; i.e., from $I_p^S$. Generally, the sensitivity of a probe will correlate with that probe's specificity. Thus, in preferred embodiments, those probes that are more specific for a target polynucleotide will also be more sensitive for that target polynucleotide.

Preferably, the analytical methods of the present invention are implemented by means of a computer system such as those described hereinbelow. FIG. 7 illustrates an exemplary computer system suitable for implementation of the analytic methods of this invention. A computer system such as the exemplary computer system 701 typically comprises one or more internal components and is linked to one or more external components. The internal components of such computer systems comprise a processor element 702 interconnected with a memory 703. For example, the computer system can be an Intel Pentium based processor of 200 MHz or greater clock rate and with 32 MB or more of main memory.

The external components include mas storage 704. The mass storage can be, e.g., one or more hard disks which are typically packaged together with the processor and the memory. Such hard disks are typically of 1 GB or greater storage capacity. Other external components include one or more user interface devices 705 which can include, for example, a monitor and a keyboard together with a pointing device 706 such as a "mouse" or other graphical input device. Typically, the computer system is also linked to a network link 707, which can be, e.g., part of an Ethernet link to one or more other local computer systems, to one or more remote computer systems or to one or more wide area communication networks such as the Internet. Such a network link allows the computer system to share data and processing tasks with other computer systems.

Loaded into the memory during operation of this system are several software components which are both standard in the art and special to the instant invention. These software components collectively cause the computer system to function according to the methods of the invention (i.e., they will cause the processor to implement the methods of the invention). The software components are typically encoded and stored on computer readable media such as the mass storage component 704. However, one or more of the software components can be encoded and stored on other forms of computer readable media, including, but not limited to, a floppy disk, a CD-ROM or a DAT tape. Software component 710 represents an operating system which is responsible for managing the computer system and its network interconnections. The operating system can be, for example, of the Microsoft Windows™ family, such as Windows 95, Windows 98, Windows 2000 or Windows NT. Alternatively, the operating system can be a Macintosh operating system or a Unix operating system such as LINUX. Software component 711 represents common languages and functions conveniently present in the system to assist programs implementing the methods specific to the present invention. Languages that can be used to program the analytic methods of the invention include, for example, C, C++ and, less preferably, FORTRAN and JAVA. Most preferably, the methods of the invention are programmed in mathematical software packages which allow symbolic entry of equations and high-level specification of processing, including specific algorithms to be used, thereby freeing a user of the need to procedurally program individual equations and algorithms. Such packages include, e.g., Matlab from Mathworks (Natick, Mass.), Mathematic from Wolfram Research (Champaign, Ill.) or S-Plus from Math Soft (Seattle, Wash.).

Accordingly, software component 712 represents analytic methods of the present invention as programmed in a procedural language or symbolic package. The software components may also include a component 713 containing data, e.g., in a database, used in the analytical methods of the invention. For example, the database component may comprise data representing the amount of binding (e.g., hybridization) of molecules in one or more samples to a probe or probes. Such (computer systems can be used to implement and practice the methods of the present invention. In particular, a user can cause execution of the analysis software component 712 of the system so that the processor implements the methods of the invention and thereby evaluates the binding of one or more probes to one or more different target molecules.

The compositions of the invention also include computer program products which can be used to load one or more of the above-described software components into the memory of a computer system and cause the processor of the computer system to implement the methods of the invention. Such computer program products generally comprise one or more computer readable storage media (e.g., floppy disks, CD-ROMS, DAT tapes) onto which one or more computer program mechanisms are embedded or encoded. In particular, the computer program mechanisms comprise, e.g., one or more of the above described software components, such that the program mechanisms can be loaded into the memory of a computer system (such as the memory of exemplary computer system 701) and cause the processor of that computer system to execute the analytical methods of the present invention.

Alternative systems and methods for implementing the analytic methods of the present invention will also be recognized by those skilled in the art and are, therefore, intended to be comprehended within the scope of the accompanying claims. For example, those skilled in the art will recognize alternative program structures which may be used, e.g., in a computer system or in a computer program product, for implementing the methods of the invention. It is therefore understood that systems and products encompassing such alternative program structures are also part of the present invention.

5.3. Applications to Probe and Microarray Design

The methods and compositions of the invention are particularly useful for the design of microarrays that have many uses, e.g., in the fields of biology and drug discovery. For example, the methods and compositions of the invention can be used to prepare microarrays of probes that are capable of screening and specifically detecting large numbers of different target polynucleotides such as a large number of different genes or gene transcripts in a cell or organism.

For example, such "screening chips," as they are referred to herein, can comprise probes capable of differentially hybridizing to and thereby detecting at least 2,000 or at least 4,000 different target polynucleotides. More preferably, such screening chips have probes capable of differentially hybridizing to and thereby detecting at least 10,000, at least 15,000, or at least 20,000 different target polynucleotides. In particularly preferred embodiments, screening chips can be prepared that have probes capable of differentially hybridizing to and thereby detecting more than 50,000, more than 80,000 or more than 100,000 different target polynucleotides.

In embodiments wherein the screening chips are used to detect polynucleotides corresponding to genes or gene transcripts of a cell or organism, such screening chips will therefore typically have probes that hybridize specifically and distinguishably to at least 50% of the genes in the genome of a cell or organism. Screening chips can more preferably have probes that hybridize specifically and distinguishably to at least 75%, at least 80%, at least 85%, at least 90%, at least 95%, or at least 99% of the genes in the genome of a cell or organism. In fact, in particularly preferred embodiments, screening chips comprise probes that hybridize specifically and distinguishably to all (i.e., 100%) of the genes in the genome of a cell or organism.

The methods and compositions of the invention can also be used to prepare microarrays of probes that are capable of specifically detecting smaller number of different target polynucleotides, but with greater sensitivity and specificity. For example, microarrays can be designed, using the methods of the present invention, that can reliably and accurately detect changes in certain genes, referred to herein as "signature genes" that change, e.g., in response to some perturbation of change to a cell or organism expressing or potentially capable of expressing those genes.

Specifically, by using the methods described hereinabove, both the sensitivity and the specificity can be determined simultaneously for a plurality of different probes. The probes can then be ranked (e.g., according to the methods described in U.S. Provisional Application Ser. No. 60/144,382 filed on Jul. 16, 1999 and U.S. patent application Ser. No. 09/364, 751 filed on Jul. 30, 1999), and then selected to select those particular probes in the plurality that have the highest sensitivity and specificity for a particular target. Such probes can then be used in microarrays, such as the screening and signature arrays or "chips" described above.

In particular, by using probes that are optimized for both sensitivity and specificity, the number of different probes required to reliably and distinguishably detect a particular polynucleotide can be greatly reduced (e.g., to as few as one probe for each target polynucleotide). Thus, microarrays can be prepared that have probes that specifically and distinguishably hybridize to a greater number of different polynucleotides. Alternatively, by using probes that are optimized for both sensitivity and specificity for a particular target, microarrays can be prepared that can more reliably and accurately detect the amount or level of certain particular target polynucleotides in a sample, or that can more reliably and accurately detect changes in the amount or level of certain particular target polynucleotides in two or more different samples. Such microarrays will therefore typically have binding sites (i.e., probes) that bind specifically and distinguishably to a small number of different polynucleotides.

The methods of the invention can readily be applied by a skilled artisan to select probes for a plurality of different target polynucleotides, e.g., by repeating the above described methods for each particular target polynucleotide in the plurality. Alternatively, in certain embodiments the methods of the invention can be used to evaluate and select probes for two or more different polynucleotides wherein the two or more different polynucleotides are sufficiently orthogonal to each other that they do not cross-hybridize to a common polynucleotide sequence. "Orthogonal" polynucleotides refers to two or more polynucleotides that contain no common nucleic acid sequences. Orthogonal sequences are not, therefore, expected to cross-hybridize. In particular, a complementary sequence that hybridizes to a first polynucleotide sequence is not expected to hybridize to a second polynucleotide sequence if the first and sequence polynucleotide sequences are orthogonal sequences. Thus, more specifically, none of the two or more different target polynucleotide molecules used in such an alternative embodiment will hybridize or cross-hybridize with a probe that also hybridizes or cross-hybridizes any of the other different target polynucleotide molecules used in the embodiment.

Sequences that are sufficiently orthogonal to use in such embodiments of the present invention are understood to be sequences that have no more than 50% sequence identity to each other, and more preferably have no more than 20%, no more than 10%, no more than 5%, no more than 2% or no more than 1% sequence identity to each other. Such sufficiently orthogonal sequences can be readily identified, e.g., by means of a sequence comparison algorithm such as the Basic Local Alignment Search Tool (BLAST) or Power BLAST algorithms to identify such sequences within a database of nucleotide sequences (e.g., within the GenBank or dbEST databases). Sequence comparison algorithms such as BLAST and PowerBLAST are well known in the art (see, e.g., Altschul et al., 1990, *J. Mol. Biol.* 215:403-410; Altschul, 1997, *Nucleic Acids Res.* 25:3389-3402; and Zhang and Madden, 1997, *Genome Res.* 7:649-656). One skilled in the relevant art(s) therefore readily appreciates that such algorithms can be used to compare polynucleotide sequences, e.g., using standard parameters that are well known in the art.

The methods of the invention can also be used to test theoretical models that predict properties such as the sensitivity and specificity of polynucleotide probes. For example, U.S. Provisional Application Ser. No. 60/144,382 filed on Jul. 16, 1999 and U.S. patent application Ser. No. 09/364,751 filed on Jul. 30, 1999 disclose methods which can be used to calculate or predict the sensitivity and specificity of a given oligonucleotide, e.g., theoretical models for the thermodynamics of polynucleotide hybridization such as the nearest neighbor model (see, e.g., SantaLucia, 1998, *Proc. Natl. Acad. Sci. U.S.A.* 95:1460-1465). Using the methods and compositions of the invention disclosed herein, hybridization properties of one or more probes such as the sensitivity and specificity can be empirically determined and compared, e.g., to the values predicted by such theoretical models. Such comparisons can then be used, e.g., to test the reliability and/or accuracy of such theoretical models, as well as to refine such models so that they are more accurate and reliable. In one preferred embodiment, the methods of the invention can be used to establish a database of properties of a plurality of different probes, such as the specificity and sensitivity of each probe to a diverse set of target polynucleotides (e.g., a diverse set of different genes or gene transcripts). Such a database is well suited to testing and training theoretical models of polynucleotide performance (e.g., predicting polynucleotide sensitivity and specificity), including the models described above and in U.S. Provisional Application Ser. No. 60/144,382 filed on Jul. 16, 1999 and in U.S. patent application Ser. No. 09/364,751 filed on Jul. 30, 1999.

6. EXAMPLE

The following example of evaluating different probe molecules is presented as an exemplary illustration of the methods and compositions of the previously described invention and is not limiting of that invention in any way. Specifically, the example presented herein describes the selection of a plurality of oligonucleotide probes and the evaluation of their sensitivity and specificity for the gene YER019W of the yeast *Saccharomyces cerevisiae*. The results presented herein demonstrate that probes which are both sensitive and specific for a particular target can be readily identified using the methods of the invention described hereinabove.

YER019W is a known gene of the yeast *Saccharomyces cerevisiae* (GenBank Accession No. U18778) that is about 1.4 kilobases in length (i.e., slightly longer than the medium length of yeast ORFs). Although the function of the gene is unknown, it has properties that make it an excellent test candidate for probe selection according to the methods of the present invention. First, the sequence of the gene is unique, with no close homologs as can be demonstrated by a routine BLAST comparison (Altschul et al., 1990, *J. Mol. Biol.* 215:403-410; Altschul, 1997, *Nucleic Acids Res.* 25:3389-3402; and Zhang and Madden, 1997, *Genome Res.* 7:649-656) of its sequence with the sequences of the yeast genome. This property renders YER019W appropriate for testing subsequence specificity against general cross-hybridization. Further, YER019W is expressed at very low levels in wild type cells (approximately one copy per cell). Thus, detection of the wild type levels of expression by hybridization requires high sensitivity probes. However, its abundance in wild type cells is not so low as to be undetectable.

Oligonucleotide probes were selected for evaluation by identifying every other 25-mer sequence complementary to the YER019W base sequence (GenBank Accession No. U18778). Thus, the candidate probes consisted of a total of 705 25-mer sequences complementary to bases 1-25, 3-27, 5-29, etc. spanning the full length of the YER019W sequence.

Three sets of control oligonucleotide probes were also selected. The first set consisted of 50 25-mer probes complementary to the yeast gene YGR192C (GenBank Accession No. Z72977), a housekeeping gene that is highly expressed in yeast (about 200 to 400 copies per cell). Thus, the probes derived from this gene served as positive controls for labeling and non-specific hybridization since signal intensity from hybridization to this probe should always be high. The second set of control probes consisted of 200 25-mer probes complementary to the yeast gene YLR040C (GenBank Accession No. Z73212), a gene of unknown function that is expressed at extremely low levels (no more than one copy per cell) in yeast. These probes thus served as positive sensitivity controls. The control probes for both the first and second sets were also selected by tiling every other position in a randomly chosen section of the gene YGR192C and YLR040C, respectively. The third set of probes consisted of 43 20-mer sequences selected from the yeast deletion consortium barcodes (see, Shoemaker et al., 1996, *Nature Genetics* 14:450-456) to be random nucleotide sequences that are not related to any naturally occurring sequences in yeast and maximally orthogonal to each other. Thus, these probes served as negative controls for hybridization of the yeast sequences.

The selected YER019W oligonucleotides, the YGR192C and YLR040C controls and the negative controls were all printed in duplicate on the top and bottom half of three chips, referred to as Chips 978, 979, and 1136, according to the standard inkjet printing techniques of Blanchard (see, e.g., International Patent Publication No. WO 98/41531, published on Sep. 24, 1998; Blanchard et al., 1996, *Biosensors and Bioelectronics* 11:687-690; Blanchard, 1998, in *Synthetic DNA Arrays in Genetic Engineering*, Vol. 20, J. K. Setlow, ed., Plenum Press, New York at pages 111-123). All chips were hybridized overnight at 66° C. in 200 μL of hybridization solution consisting of 10 mM Tris pH 7.6, 1 M NaCl, 1% Triton-X-100; 1 μg/μL bovine serum albumin, 0.1

µg/µL sheared herring sperm DNA, 50 µM Cy3-labeled gridline oligonucleotide, and 50 µM Cy5-labeled gridline oligonucleotide. After hybridization, the chips were washed by shaking for 10 seconds at room temperature in 6×SSPE, 0.005% Triton-X-100; and for another 10 seconds at room temperature in 0.06×SSPE. The chips were dried with pressurized air, and scanned using a General Scanning 3000 confocal laser scanner.

Chips 978 and 979 were hybridized simultaneously with differentially labeled samples. The first sample consisted of fluorescently labeled 1.6 ng fragmented YER019W cRNA and served as a specific hybridization sample. This concentration of YER019W RNA corresponds to approximately 10 copies of the YER019W transcript per cell or about 10 times the natural abundances of YER019W. The second sample, which served as a non-specific hybridization sample, consisted of 2 µg fluorescently labeled fragmented cRNA from yer019w/- (i.e., a diploid yeast strain specifically deleted for the gene YER019W) homozygous disruption yeast mRNA. Specifically, chip 978 was hybridized with Cy5 labeled YER019W cRNA and Cy3 labeled yer019w/- cRNA. Chip 979 was hybridized with Cy3 labeled YER019W cRNA and Cy5 labeled yer019w/- cRNA. Chip 1136 was hybridized with 2 µg Cy5 labeled fragmented cRNA from wild type yeast and with 2 µg Cy3 labeled fragmented cRNA from yer019w/-.

Figures 4A, 4B:
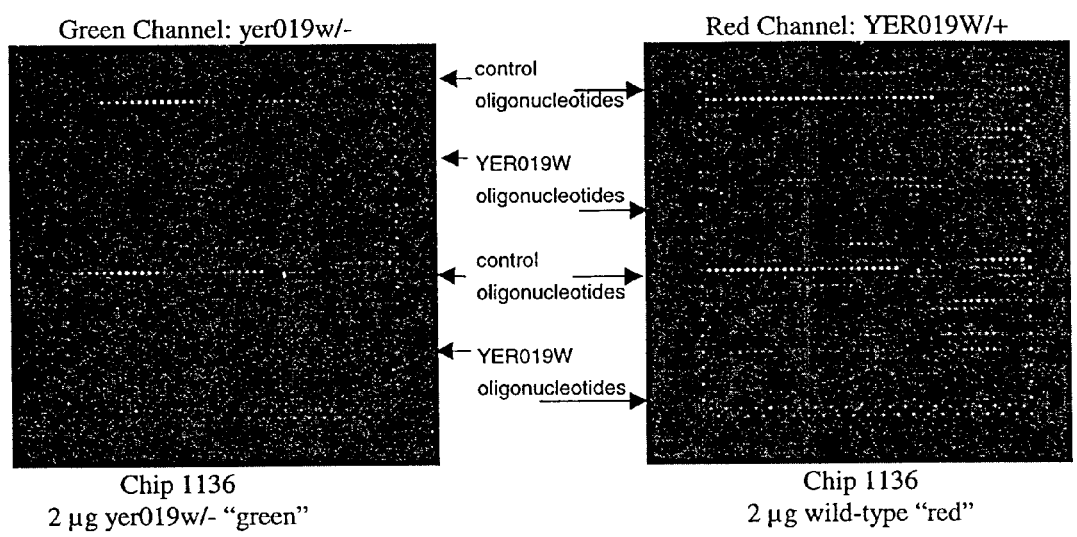
FIGS. 4A-4B show fluorescence intensity images from the simultaneous hybridization of two samples to a microarray identical to the array in FIGS. 2A-2B.

Combined color images of the three chips 978, 979 and 1136 are shown in FIGS. 2-4, respectively. Each of the two hybridization samples can be distinguished by the different fluorescence color of their respectively labels: Cy3 which fluoresces "green" (FIGS. 2A, 3A and 4A), and Cy5 which fluoresces "red" (FIGS. 2B, 3B and 4B).

The gene specific signal (i.e., from the specific hybridization sample, YER019W) from these images was combined from chips 978 and 979. A plot of the combined signal versus the gene tiling position is provided in FIG. 5A. Likewise, the non-specific signal (i.e., from the non-specific hybridization sample, yer019w/-) was also combined from chips 978 and 979 and is plotted versus the gene tiling positions in FIG. 5B.

The signal depicted in FIG. 5A is an indicator of the sensitivity of each probe from the gene YER019W. Specifically, peaks in the plot shown in FIG. 5A indicate probes that hybridize well (i.e., are sensitive) to YER019W and might therefore be desirable probes for detecting that gene in a polynucleotide sample. The signal depicted in FIG. 5B indicates the amount of cross-hybridization. Peaks in this plot indicate probes that cross-hybridize with other polynucleotide sequences, suggesting that they would be undesirable for specifically detecting the YER019W sequence, especially in a sample comprising many different polynucleotide sequences (e.g., a sample of many different yeast polynucleotide sequences extracted from a cell or cells). FIG. 5C shows a plot of the ratio between the gene specific (i.e., YER019W) signal in FIG. 5A and the gene non-specific (i.e., yer019w/-) signal in FIG. 5B. The plot therefore indicates the specificity of each probe. Peaks in this plot indicate probes that hybridize well to YER019W while at the same time exhibiting only limited cross-hybridization to other polynucleotides. The data in FIGS. 5A and 5C also indicate that, in general, the sensitivity and specificity may be well-correlated.

A scatter plot is shown in FIG. 6 that diagrams relationships between the sensitivity (GS signal, horizontal axis) and specificity (GS/GNS signal, vertical axis) for each complementary probe of YER019W using the data in FIGS. 5A and 5C. Those probes having both high sensitivity and specificity (i.e., in the upper right hand corner of the scatter plot) are particularly desirable probes for use, e.g., in a microarray to detect the YER019W gene in a sample of many different genes and/or gene transcripts. Such desirable probes are also indicated by an (x) in FIG. 5C.

Thus, the methods and compositions described hereinbelow allow for the selection of the most specific and sensitive probes for detecting a particular polynucleotide (e.g., a particular gene).

7. REFERENCES CITED

All references cited herein are incorporated herein by reference in their entirety and for all purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled.

What is claimed is:

1. A method for evaluating a binding property of a polynucleotide probe to a target nucleotide sequence, said polynucleotide probe comprising a predetermined nucleotide base sequence that is complementary to at least a hybridizable portion of said target nucleotide sequence, said method comprising determining a ratio of the amount of hybridization of polynucleotides in a first sample to the polynucleotide probe and the amount of hybridization of polynucleotides in a second sample to the polynucleotide probe, wherein:

(a) the first sample comprises a plurality of polynucleotide molecules comprising said target nucleotide sequence; and (b) the second sample comprises a plurality of different polynucleotide molecules wherein each different polynucleotide molecule comprises a sequence that is different from the nucleotide sequences of any other polynucleotide molecules in said plurality of different polynucleotide molecules, wherein at least 75% of the polynucleotide molecules in said first sample are polynucleotide molecules comprising said target nucleotide sequence, and wherein said ratio is used as a measure of said binding property, thereby evaluating said binding property of said polynucleotide probe.

2. The method of claim 1 wherein the target nucleotide sequence in the first sample is a nucleotide sequence from a gene or gene transcript of a cell or organism, or of an mRNA, cDNA or cRNA derived therefrom.

3. The method of claim 1 wherein the plurality of different polynucleotide molecules in the second sample comprises nucleotide sequences from a plurality of genes or gene transcripts of a cell or organism.

4. The method of claim 1 wherein at least 90% of the polynucleotide molecules in said first sample are said polynucleotide molecules comprising said target nucleotide sequence.

5. The method of claim 4 wherein at least 95% of the polynucleotide molecules in said first sample are said polynucleotide molecules comprising said target nucleotide sequence.

6. The method of claim 5 wherein at least 99% of the polynucleotide molecules in said first sample are said polynucleotide molecules comprising said target nucleotide sequence.

7. The method of claim 1 wherein each different polynucleotide molecule in the second sample does not comprise the target nucleotide sequence.

8. The method of claim 7 wherein:
(a) the target nucleotide sequence in the first sample is a sequence from a gene or gene transcript of a cell or organism; and
(b) the second sample comprises a polynucleotide sample from a deletion mutant of the cell or organism,
wherein the deletion mutant of the cell or organism does not express the gene or gene transcript.

9. The method of claim 1 wherein the plurality of different polynucleotide molecules in the second sample comprises:
(a) polynucleotide molecules comprising the target nucleotide sequence, and
(b) a plurality of different polynucleotide molecules, each comprising a different nucleotide sequence and each not comprising the target nucleotide sequence.

10. The method of claim 9 wherein:
(a) the target nucleotide sequence is a sequence from a gene or gene transcript of a cell or organism; and
(b) the second sample comprises a polynucleotide sample from a wild-type strain of the cell or organism,
wherein the wild-type strain of the cell or organism expresses the gene or gene transcript.

11. The method of claim 1 wherein:
(a) the first sample further comprises polynucleotide molecules that do not comprise the target nucleotide sequence; and
(b) the second sample lacks said polynucleotide molecules comprising said target nucleotide sequence.

12. The method of claim 11 wherein:
(a) the target nucleotide sequence is a sequence from a gene or gene transcript of a cell or organism;
(b) the first sample comprises a polynucleotide sample from a wild-type strain of the cell or organism which expresses the gene or gene transcript; and
(c) the second sample comprises a polynucleotide sample from a deletion mutant of the cell or organism which does not express the gene or gene transcript.

13. The method of claim 1 wherein
(a) the first sample further comprises polynucleotide molecules that do not comprise the target nucleotide sequence; and
(b) the second sample comprises:
(i) polynucleotide molecules comprising the target nucleotide sequence, and
(ii) a plurality of different polynucleotide molecules, each different polynucleotide molecule comprising a different nucleotide sequence and not comprising the target nucleotide sequence,
wherein the amount of polynucleotide molecules in the first sample comprising the target nucleotide sequence differs by at least a factor of two from the amount of polynucleotide molecules in the second sample comprising the target nucleotide sequence.

14. The method of claim 13 wherein the amount of polynucleotide molecules in the first sample comprising the target nucleotide sequence differs from the amount of polynucleotide molecules in the second sample comprising the target nucleotide sequence by at least a factor of four.

15. The method of claim 13 wherein the amount of polynucleotide molecules in the first sample comprising the target nucleotide sequence differs from the amount of polynucleotide molecules in the second sample comprising the target nucleotide sequence by at least a factor of eight.

16. The method of claim 13 wherein the amount of polynucleotide molecules in the first sample comprising the target nucleotide sequence differs from the amount of polynucleotide molecules in the second sample comprising the target nucleotide sequence by at least a factor of twenty.

17. The method of claim 13 wherein the amount of polynucleotide molecules in the first sample comprising the target nucleotide sequence differs from the amount of polynucleotide molecules in the second sample comprising the target nucleotide sequence by at least a factor of 100.

18. The method of claim 13 wherein each said polynucleotide molecule that does not comprise the target nucleotide sequence in the first sample is present in the second sample in an amount that differs from the amount of said polynucleotide molecule in the first sample by no more than a factor of 100.

19. The method of claim 13 wherein each said polynucleotide molecule that does not comprise the target nucleotide sequence in the first sample is present in the second sample in an amount that differs from the amount of said polynucleotide molecule in the first sample by no more than a factor of 10.

20. The method of claim 13 wherein each said polynucleotide molecule that does not comprise the target nucleotide sequence in the first sample is present in the second sample in an amount that differs from the amount of said polynucleotide molecule in the first sample by no more than 50%.

21. The method of claim 13 wherein the mean abundance of the polynucleotide molecules that do not comprise the target nucleotide sequence in the first sample differs from the mean abundance of the different polynucleotide molecules that do not comprise the target nucleotide sequence in the plurality of different polynucleotide molecules of the second sample by no more than a factor of two.

22. The method of claim 13 wherein the mean abundance of the polynucleotide molecules that do not comprise the target nucleotide sequence in the first sample differs from the mean abundance of the different polynucleotide molecules that do not comprise the target nucleotide sequence in the plurality of different polynucleotide molecules of the second sample by no more than 50%.

23. The method of claim 13 wherein the mean abundance of the polynucleotide molecules that do not comprise the target nucleotide sequence in the first sample differs from the mean abundance of the different polynucleotide molecules that do not comprise the target nucleotide sequence in the plurality of different polynucleotide molecules of the second sample by no more than 10%.

24. The method of claim 13 wherein the mean abundance of the polynucleotide molecules that do not comprise the target nucleotide sequence in the first sample differs from the mean abundance of the different polynucleotide molecules that do not comprise the target nucleotide sequence in the plurality of different polynucleotide molecules of the second sample by no more than 1%.

25. The method of claim 1 wherein the polynucleotide molecules in the first sample are detectably labeled.

26. The method of claim 1 wherein the polynucleotide molecules in the second sample are detectably labeled.

27. The method of claim 25 or 26 wherein the polynucleotide molecules are labeled with a fluorescent molecule.

28. The method of claim 1 wherein:
(a) the polynucleotide molecules in the first sample are labeled with a first label; and (b) the polynucleotide molecules in the second sample are labeled with a second label, the first label being distinguishable from the second label.

29. The method of claim 28 wherein:
the first label is a first fluorescent molecule, and
the second label is a second fluorescent molecule.

30. The method of claim 1 wherein the polynucleotide probe is attached to a surface of a support.

31. The method of claim 1 wherein the polynucleotide probe is one of a plurality of polynucleotide probes.

32. The method of claim 31 wherein the plurality of polynucleotide probes comprises polynucleotide probes in an array of polynucleotide probes,
said array having a support with at least one surface and different polynucleotide probes attached to said surface,
wherein each of said different polynucleotide probes attached to said surface is attached to the surface of the support in a different location.

33. The method of claim 1 wherein:
polynucleotides in the first sample are labeled with a first label and polynucleotides in the second sample are labeled with a second label that is distinguishable from the first label;
and further comprising, prior to said step of comparing the steps of:
(i) concurrently contacting the polynucleotide probe with the first sample and the second sample under conditions conducive to hybridization, and
(ii) detecting any binding that occurs between the polynucleotide probe and polynucleotides in the first sample and the second sample.

34. The method of claim 33 wherein the second sample lacks polynucleotide molecules of said first sample.

35. A method for evaluating a binding property of a plurality of polynucleotide probes to a target nucleotide sequence, wherein each polynucleotide probe in the plurality of polynucleotide probes comprises a different predetermined nucleotide base sequence that is complementary to at least a hybridizable portion of said target nucleotide sequence, said method comprising determining for each said polynucleotide probe a ratio of the amount of hybridization of polynucleotides in a first sample to said polynucleotide probe and the amount of hybridization of polynucleotides in a second sample to said polynucleotide probe, wherein:
(a) the first sample comprises a plurality of polynucleotide molecules comprising said target nucleotide sequence; and
(b) the second sample comprises a plurality of different polynucleotide molecules wherein each different polynucleotide molecule comprises a nucleotide sequence that is different from nucleotide sequence of any other polynucleotide molecules in said plurality of different polynucleotide molecules,
wherein at least 75% of the polynucleotide molecules in said first sample are polynucleotide molecules comprising said target nucleotide sequence, and wherein said ratio is used as a measure of said binding property, thereby evaluating said binding property of each said polynucleotide probe.

36. The method of claim 35 wherein each polynucleotide probe in the plurality of polynucleotide probes is attached to a surface of a support.

37. The method of claim 35 wherein the plurality of polynucleotide probes comprises polynucleotide probes in an array of probes,
said array having a support with at least one surface and different polynucleotide probes attached to said surface,
wherein each of said different polynucleotide probes attached to said surface in the plurality of probes is attached to the surface of the support in a different location.

38. The method of claim 35 wherein the first sample comprises two or more different polynucleotide molecules wherein none of the two or more different polynucleotide molecules hybridizes or cross-hybridizes to a probe that also hybridizes or cross-hybridizes to another one of the two or more different polynucleotide molecules.

39. The method of any one of claims 1, 2, 3, 4-11, 12-24, 27-35, 36-38 and 33-34, wherein said polynucleotide molecules comprising said target nucleotide sequence are the same polynucleotide molecule.

40. A method for evaluating a binding property of a plurality of polynucleotide probes to a target nucleotide sequence, said method comprising determining for each said polynucleotide probe a ratio of the amount of hybridization of polynucleotides in a first sample to said polynucleotide probe and the amount of hybridization of polynucleotides in a second sample to said polynucleotide probe, wherein:
(a) said first sample comprises a plurality of polynucleotide molecules comprising said target nucleotide sequence and a plurality of polynucleotide molecules that do not comprise the target nucleotide sequence; and
(b) said second sample comprises a plurality of different polynucleotide molecules wherein each different polynucleotide molecule comprises a sequence that is different from the nucleotide sequence of any other polynucleotide molecule in said plurality of different polynucleotide molecules, and wherein each different polynucleotide molecule in the second sample does not comprise the target nucleotide sequence,
wherein each polynucleotide probe in the plurality of polynucleotide probes comprises a different predetermined nucleotide base sequence that is complementary to at least a hybridizable portion of said target nucleotide sequence and wherein said ratio is used as a measure of said binding property, thereby evaluating said binding property of said plurality of polynucleotide probes.

41. The method of claim 40 wherein:
(a) said target nucleotide sequence is a sequence from a gene or gene transcript of a cell or organism;
(b) said first sample comprises a polynucleotide sample from a wild-type strain of the cell or organism which expresses the gene or gene transcript; and
(c) said second sample comprises a polynucleotide sample from a deletion mutant of the cell or organism that does not express the gene or gene transcript.

42. A method for evaluating a binding property of a plurality of polynucleotide probes to a target nucleotide sequence, said method comprising determining for each of said polynucleotide probes a ratio of the amount of hybridization of polynucleotides in a first sample to said polynucleotide probe and the amount of hybridization of polynucleotides in a second sample to said polynucleotide probe, wherein:
(a) said first sample comprises a plurality of polynucleotide molecules comprising said target nucleotide sequence and a plurality of polynucleotide molecules that do not comprise the target nucleotide sequence; and (b) said second sample comprises a plurality of different polynucleotide molecules wherein each different polynucleotide molecule comprises a sequence that is different from the nucleotide sequence of any other polynucleotide molecule in said plurality of different polynucleotide molecules, wherein each polynucleotide probe in the plurality of polynucleotide probes comprises a different predetermined nucleotide base sequence that is complementary to at least a hybridizable portion of said target nucleotide sequence and wherein said ratio is used as a measure of said binding property, thereby comparing said binding property of said plurality of polynucleotide probes.

43. The method of claim 42 wherein:
   (a) said target nucleotide sequence comprises a sequence from a gene or gene transcript of a cell or organism; and
   (b) said second sample comprises a polynucleotide sample from a wild-type strain of said cell or organism, wherein the wild-type strain of the cell or organism expresses the gene or gene transcript.

44. The method of claim 42, wherein said second sample comprises:
   (b1) polynucleotide molecules comprising the target nucleotide sequence, and
   (b2) a plurality of different polynucleotide molecules, each different polynucleotide molecule comprising a different nucleotide sequence and not comprising the target nucleotide sequence, and wherein the amount of polynucleotide molecules in said first sample comprising the target nucleotide sequence differs by at least a factor of two from the amount of polynucleotide molecules in said second sample comprising the target nucleotide sequence.

45. The method of claim 44 wherein the amount of polynucleotide molecules in said first sample comprising said target nucleotide sequence differs from the amount of polynucleotide molecules in said second sample comprising said target nucleotide sequence by at least a factor of four.

46. The method of claim 44 wherein the amount of polynucleotide molecules in said first sample comprising said target nucleotide sequence differs from the amount of polynucleotide molecules in said second sample comprising said target nucleotide sequence by at least a factor of eight.

47. The method of claim 44 wherein the amount of polynucleotide molecules in said first sample comprising said target nucleotide sequence differs from the amount of polynucleotide molecules in said second sample comprising said target nucleotide sequence by at least a factor of twenty.

48. The method of claim 44 wherein the amount of polynucleotide molecules in said first sample comprising said target nucleotide sequence differs from the amount of polynucleotide molecules in said second sample comprising said target nucleotide sequence by at least a factor of 100.

49. The method of claim 44 wherein each said polynucleotide molecule that does not comprise said target nucleotide sequence in said first sample is present in said second sample in an amount that differs from the amount of said polynucleotide molecule in the first sample by no more than 50%.

50. The method of claim 44 wherein the mean abundance of the polynucleotide molecules that do not comprise the target nucleotide sequence in the first sample differs from the mean abundance of the different polynucleotide molecules that do not comprise the target nucleotide sequence in the plurality of different polynucleotide molecules of the second sample by no more than a factor of two.

51. The method of claim 44 wherein the mean abundance of the polynucleotide molecules that do not comprise the target nucleotide sequence in the first sample differs from the mean abundance of the different polynucleotide molecules that do not comprise the target nucleotide sequence in the plurality of different polynucleotide molecules of the second sample by no more than 50%.

52. The method of claim 44 wherein the mean abundance of the polynucleotide molecules that do not comprise the target nucleotide sequence in the first sample differs from the mean abundance of the different polynucleotide molecules that do not comprise the target nucleotide sequence in the plurality of different polynucleotide molecules of the second sample by no more than 10%.

53. The method of claim 44 wherein the mean abundance of the polynucleotide molecules that do not comprise the target nucleotide sequence in the first sample differs from the mean abundance of the different polynucleotide molecules that do not comprise the target nucleotide sequence in the plurality of different polynucleotide molecules of the second sample by no more than 1%.

* * * * *